US008338660B2

(12) United States Patent
Gagliardi et al.

(10) Patent No.: US 8,338,660 B2
(45) Date of Patent: Dec. 25, 2012

(54) ABSORBENT ARTICLE COMPRISING AN ABSORBENT ELEMENT COMPRISING A LIQUID ABSORBENT THERMOPLASTIC COMPOSITION

(75) Inventors: Ivano Gagliardi, Pescara (IT); Paolo Veglio, Pescara (IT); Roberto D'Addario, Pianella (IT); Giovanni Carlucci, Chieti (IT); Marco Digiacomantonio, Foggia (IT)

(73) Assignee: The Procter & Gamble Company, Cincinnati, OH (US)

( * ) Notice: Subject to any disclaimer, the term of this patent is extended or adjusted under 35 U.S.C. 154(b) by 334 days.

(21) Appl. No.: 12/771,401

(22) Filed: Apr. 30, 2010

(65) Prior Publication Data

US 2010/0211037 A1 Aug. 19, 2010

Related U.S. Application Data

(63) Continuation of application No. 10/669,610, filed on Sep. 23, 2003, now Pat. No. 7,736,349.

(30) Foreign Application Priority Data

Sep. 24, 2002 (EP) .................................... 02021371

(51) Int. Cl.
A61F 13/15 (2006.01)
A61F 13/20 (2006.01)
(52) U.S. Cl. ........................................ 604/368; 604/370
(58) Field of Classification Search ............ 604/367–370
See application file for complete search history.

(56) References Cited

U.S. PATENT DOCUMENTS

| | | |
|---|---|---|
| 3,156,242 A | 11/1964 | Crowe, Jr. |
| 3,929,135 A | 12/1975 | Thompson |
| 3,989,867 A | 11/1976 | Sisson |
| 4,310,593 A | 1/1982 | Gross |
| 4,324,246 A | 4/1982 | Mullane |
| 4,342,314 A | 8/1982 | Radel |
| 4,463,045 A | 7/1984 | Ahr |
| 4,591,523 A | 5/1986 | Thompson |
| 4,609,518 A | 9/1986 | Curro |
| 4,629,643 A | 12/1986 | Curro |
| 4,637,819 A | 1/1987 | Ouellette |
| 4,654,039 A | 3/1987 | Brandt |
| RE32,649 E | 4/1988 | Brandt |
| 4,950,254 A | 8/1990 | Anderson |
| 4,995,333 A | 2/1991 | Keller et al. |
| 5,006,394 A | 4/1991 | Baird |
| 5,009,653 A | 4/1991 | Osborn, III |
| 5,175,046 A | 12/1992 | Nguyen |
| 5,433,715 A | 7/1995 | Tanzer |
| 5,591,510 A | 1/1997 | Junker |
| 5,597,811 A | 1/1997 | Gruber |
| 5,621,088 A | 4/1997 | Gruber |
| D394,503 S | 5/1998 | Perrini |
| 5,755,710 A | 5/1998 | Menard |
| 5,810,800 A | 9/1998 | Hunter et al. |
| 5,855,719 A | 1/1999 | Menard |
| 5,895,379 A | 4/1999 | Litchholt et al. |
| 5,961,505 A | 10/1999 | Coe et al. |
| 6,015,608 A | 1/2000 | Koslow |
| 6,140,550 A | 10/2000 | Beihoffer et al. |
| 6,403,857 B1 | 6/2002 | Gross et al. |
| 6,458,877 B1 | 10/2002 | Ahmed et al. |
| 6,465,379 B1 | 10/2002 | Cook et al. |
| 6,495,612 B1 | 12/2002 | Corzani et al. |
| 6,498,201 B1 | 12/2002 | Corzani et al. |
| 6,534,572 B1 | 3/2003 | Ahmed et al. |
| 6,562,742 B2 | 5/2003 | Dutkiewicz et al. |
| 6,677,394 B1 | 1/2004 | Butterbach et al. |
| 6,822,135 B2 | 11/2004 | Soerens et al. |
| 2001/0014797 A1 | 8/2001 | Suzuki et al. |
| 2002/0039869 A1 | 4/2002 | Achille |
| 2003/0012928 A1 | 1/2003 | Malowaniec et al. |
| 2003/0040729 A1 | 2/2003 | Malowaniec et al. |
| 2003/0065299 A1 | 4/2003 | Carlucci et al. |
| 2003/0093051 A1 | 5/2003 | Malowaniec et al. |
| 2003/0109628 A1 | 6/2003 | Bonfanti et al. |
| 2003/0113548 A1 | 6/2003 | Corzani et al. |
| 2003/0120233 A1 | 6/2003 | Ohshima et al. |
| 2003/0171464 A1 | 9/2003 | Corzani et al. |
| 2004/0058159 A1 | 3/2004 | Gagliardi et al. |
| 2004/0059018 A1 | 3/2004 | Gagliardi et al. |
| 2004/0065232 A1 | 4/2004 | Lykke |
| 2004/0127883 A1 | 7/2004 | Cowell et al. |
| 2005/0215967 A1 | 9/2005 | Toro et al. |
| 2005/0273067 A1 | 12/2005 | Malowaniec et al. |

FOREIGN PATENT DOCUMENTS

DE 100 26 861 A 12/2001

(Continued)

OTHER PUBLICATIONS

US 5,718,918, 02/1998, Rieker (withdrawn)

*Primary Examiner* — Melanie Hand
(74) *Attorney, Agent, or Firm* — Andrew J. Hagerty

(57) ABSTRACT

The present invention relates to absorbent articles, typically for feminine protection, including a topsheet, a backsheet and an absorbent element positioned between the tospheet and the backsheet, said absorbent element includes a fluid storage layer which a liquid absorbent thermoplastic composition. The absorbent thermoplastic composition is a polymeric base material having particles of water-insoluble water-swellable absorbent material dispersed therein. The liquid absorbent thermoplastic composition is configured in a plurality of unattached spaced apart zones.

20 Claims, 9 Drawing Sheets

FOREIGN PATENT DOCUMENTS

| | | |
|---|---|---|
| EP | 0 130 848 A2 | 1/1985 |
| EP | 0 134 086 A1 | 3/1985 |
| EP | 0 523 719 A1 | 1/1993 |
| EP | 0 612 233 B1 | 4/1996 |
| EP | 0 349 241 B1 | 8/1996 |
| EP | 0 523 683 B1 | 9/1996 |
| EP | 1 013 291 A1 | 6/2000 |
| EP | 1013291 A1 * | 6/2000 |
| EP | 0 766 953 B1 | 9/2000 |
| GB | 2076491 A | 12/1981 |
| GB | 2087071 A | 5/1982 |
| GB | 2184 389 A | 6/1987 |
| GB | 2184 390 A | 6/1987 |
| GB | 2184 391 A | 6/1987 |
| WO | WO 96/09023 A1 | 3/1996 |
| WO | WO 96/16624 A2 | 6/1996 |
| WO | WO 97/03795 | 2/1997 |
| WO | WO 97/03818 A1 | 2/1997 |
| WO | WO 97/24097 A1 | 7/1997 |
| WO | WO 98/07618 A1 | 2/1998 |
| WO | WO 99/57201 | 11/1999 |
| WO | WO 02/07791 | 1/2002 |

* cited by examiner

ABSORBENT ARTICLE COMPRISING AN ABSORBENT ELEMENT COMPRISING A LIQUID ABSORBENT THERMOPLASTIC COMPOSITION

CROSS REFERENCE TO RELATED APPLICATION

This application is a continuation of U.S. application Ser. No. 10/669,610 filed Sep. 23, 2003 now U.S. Pat. No. 7,736,349.

FIELD OF THE INVENTION

The present invention relates to absorbent articles in particular articles for feminine protection like sanitary napkins and panty liners, which comprise an absorbent element comprising a liquid absorbent thermoplastic composition comprising a thermoplastic polymeric base material having particles of water-insoluble water swellable absorbent material dispersed therein, the liquid absorbent thermoplastic composition being configured in a plurality of unattached spaced apart zones.

BACKGROUND OF THE INVENTION

Although absorbent articles, such as sanitary napkins or panty liners, have improved a lot the last years with respect to various features like protection and comfort in use, there is still a consumer need for further improvements in these two directions.

Indeed, there exists a real consumer need for absorbent articles, typically for feminine protection articles, having improved liquid handling properties, namely enhanced liquid distribution properties and a liquid capacity high enough for use without consumer fears of leakage or staining especially after prolonged period of wearing time, yet which are thin and flexible, thereby offering enhanced fit and comfort.

It is thus an object of the present invention to provide absorbent articles, preferably those for feminine protection, which provide enhanced distribution, absorption and retention of body fluid not only upon first contact with body fluid discharge but also upon additional subsequent body fluid discharge, thereby making the wearing experience more pleasant over prolonged period of time, and hence improving comfort. It is another object of the present invention to provide such a feminine protection article which further promotes a continuously self-conforming anatomical cooperation of the article to the wearer during various activities (e.g. sport). It is an additional object of the present invention to provide such a feminine protection article which further offers enhanced fit, comfort and a low degree of awareness.

It has now been found that all above mentioned objects are met by providing absorbent articles, like sanitary napkins and panty liners, comprising a topsheet, a backsheet and an absorbent element positioned between said topsheet and said backsheet, said element comprising a storage layer which comprises a liquid absorbent thermoplastic composition. This composition comprises a polymeric base material having particles of water-insoluble water swellable absorbent material dispersed therein, said composition is configured in a plurality of unattached spaced apart zones.

In one embodiment herein the liquid absorbent thermoplastic composition has a total absorption capacity towards saline solution of at least 2 grams/gram. In another embodiment herein the liquid absorbent thermoplastic composition represents at least 15% by weight of the total weight of the absorbent element. Most preferred executions herein combine this two features.

Advantageously the absorbent articles of the present invention comprising a storage layer with said unattached spaced apart zones of liquid absorbent thermoplastic composition exhibit faster and enhanced fluid distribution as well as enhanced fluid acquisition and retention, this not only upon first contact with body fluid but also especially when submitted to subsequent body fluid discharge versus absorbent articles being different from the ones of the present invention only in that they comprise a storage layer made of the same liquid absorbent thermoplastic composition but configured in continuous manner (e.g., covering in continuous manner almost the whole surface area between the topsheet and backsheet of the article) as opposed to discontinuous. The interstitial area between the unattached spaced apart zones of liquid absorbent thermoplastic composition (also called herein transport regions) facilitate and promote the flow of body fluid towards said unattached zones as well as the absorption of body fluid by said zones. In other words, once body fluid reaches the absorbent element, namely the storage layer, the distribution speed of the body fluid between the unattached zones is higher than the absorbency speed of the water swellable absorbent material comprised in said zones, resulting thereby in faster and enhanced distribution of fluid in the so-called transport regions of the article. Without to be bound by any theory it is believed that this is due to the low absorption kinetic of the absorbent material being entrapped into the polymeric base material in comparison to free absorbent material. When the absorption speed of absorbent material becomes predominant versus the distribution speed of the fluid in the so called transport regions, the fluids are absorbed by the absorbent material in the unattached spaced apart zones, thereby lowering the amount of fluid present in the transport regions and even emptying said regions. Hence upon subsequent discharge of body fluid within the article, the transport regions are able to fulfill once more their function of fluid distribution, resulting in more effective use of total amount of absorbent material present in the article. Indeed the gel blocking phenomenon is reduced and hence a better use of total absorption capacity of the absorbent material is obtained according to the present invention. Actually it has surprisingly been found that the fluid acquisition upon subsequent body fluid discharge in the article of the present invention is equal or even better than upon first fluid discharge. Without to be bound by theory it is believed that after the first body fluid discharge the absorbent element, namely storage layer, due to its outstanding fluid distribution properties towards increased effective total surface area used in the article per the so called transport regions and effective fluid absorption and retention properties of the storage zones becomes wetted upon enlarged surface area, hence more hydrophilic resulting in overall more effective fluid acquisition upon subsequent fluid discharge. In other words, the subsequent body fluid discharge triggers the acquisition capacity and speed, the absorbent material being much more available to absorb fluid.

Advantageously the present invention allows for versatility in positioning of the plurality of unattached spaced apart zones of said liquid absorbent thermoplastic composition. Indeed the present invention allows to target the position of the plurality of unattached spaced apart zones and hence of the absorbent material where needed in the absorbent element/article and hence optimizes the ratio total amount of absorbent material and liquid absorption capacity. The total amount of particles of water-insoluble water swellable absorbent material present in said spaced apart zones of the absorbent element will be more efficiently utilized resulting in improved absorption characteristics of the absorbent element. As a result, the absorbent article can be configured with a thinner structure which is capable of absorbing larger amount of body fluid and more flexible structure. The thinner and more flexible structure can in turn provide improved fit and comfort to the wearer.

Advantageously the absorbent element, namely storage layer, of the articles of the present invention delivers outstanding protection with absence of water swellable absorbent material particle spillage in both dry and wet condition. The powder spillage free property of the thermoplastic composition used herein is beneficial for easier processability and handling in plant as well as for safety criteria. Also the swollen absorbent material in wet condition is less liable to escape the spaced apart zones of the storage layer. Without to be bound by theory it is speculated that cohesion of polymeric base material is able to maintain location of the absorbent materials also after swelling, thereby accommodating the increased volume of the swollen material.

Advantageously the use of the liquid absorbent thermoplastic composition herein fulfill besides the absorption properties also the function of adhering adjacent/surrounding layers of the article together. Hence the need of conventional adhesive glue to adhere storage layer to adjacent layers for example backsheet and topsheet can be avoided.

In an embodiment herein wherein the backsheet of the article is a breathable backsheet, it has been found that the absorbent element according to the present invention, especially for those embodiments wherein the absorbent element comprises, as the storage layer, the liquid absorbent thermoplastic composition described herein configured in a plurality of unattached spaced apart zones, is particularly advantageous as besides above mentioned benefits, its use also results in improved air and water vapor permeability of the absorbent article both in dry and wet condition.

BACKGROUND ART OF THE INVENTION

Compositions comprising a thermoplastic component and a super absorbent polymer are known from the art. For example WO99/57201 or WO02/07791 describe such compositions and their applications to bond different layers of conventional disposable absorbent articles such as diapers, feminine napkins and medical dressings. EP-A-1 013 291 discloses a hot melt adhesive with super absorbent polymers. The resulting thermoplastic hot-melt adhesive material can be used to adhesively bond substrates such as polymeric films together, as well as to provide additional liquid absorption capacity to absorbent structures. This adhesively coated material is particularly useful in the construction of absorbent products such as catamenials. Absorbent articles which include super absorbent material located in discrete pockets having water-sensitive and water-insensitive containment structures are known from U.S. Pat. No. 5,433,715.

None of these prior art references discloses nor suggests absorbent articles, namely hygienic disposable articles for feminine protection, comprising an absorbent element with storage layer comprising a liquid absorbent thermoplastic composition as presently claimed.

SUMMARY OF THE INVENTION

The present invention encompasses absorbent article, typically for feminine protection, comprising a topsheet, a backsheet and an absorbent element positioned between said topsheet and said backsheet, said element comprising a storage layer comprising a liquid absorbent thermoplastic composition which comprises a polymeric base material having particles of water-insoluble water swellable absorbent material dispersed therein, said composition being configured in a plurality of unattached spaced apart zones. In one execution the composition has a total absorption capacity towards saline solution of at least 2 g/g. In another execution the composition represents at least 15% by weight of the total weight of the absorbent element.

All documents cited are, in relevant part, incorporated herein by reference; citation of any document is not to be construed as an admission that it is prior art with respect to the present invention.

DETAILED DESCRIPTION OF THE INVENTION

Figure 1:
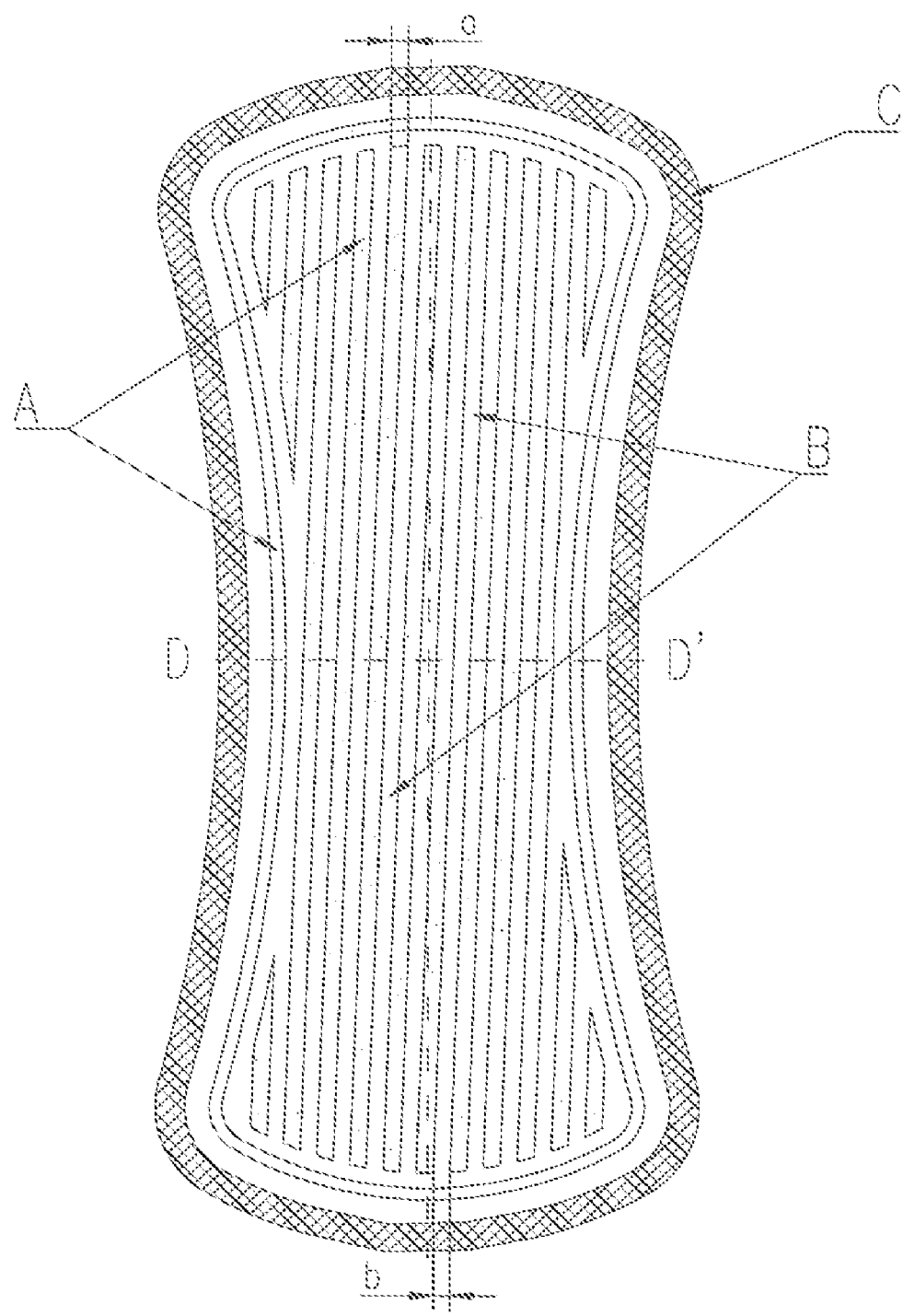
FIG. 1 shows a top plan view of the garment facing surface of a panty liner according to the present invention having an absorbent element with a storage layer made of a liquid absorbent thermoplastic composition as described herein in a multi stripe pattern.

The term "absorbent article" is used herein in a very broad sense including any article able to receive and/or absorb and/or contain and/or retain fluids and/or exudates, especially body fluids/body exudates. "Absorbent articles" as referred to herein include, without to be limited to, sanitary napkins, panty liners, incontinence pads, interlabial pads, breast pads, sweat-absorbent underarm pads, collar inserts, baby diapers, adult incontinence diapers, and human waste management devices.

The term "disposable" is used herein to describe articles that are not intended to be launched or otherwise restored or reused as an article (i.e., they are intended to be discarded after a single use and, preferably to be recycled, composted or otherwise disposed of in an environmentally compatible manner).

As used herein, the term 'wearer-facing' surface refers to the surface of the component of the article generally oriented to face the wearer skin and/or mucosal surface during use of the article. As used herein, the term 'garment facing' surface refers to the opposite outer surface of the article, typically the surface directly facing the garment of a wearer, if worn in direct contact with garment.

As used herein, the term 'body fluids' refers to any fluid produced by human body occurring naturally including for instance perspiration, urine, menstrual fluids, vaginal secretions and the like, or accidentally like for instance in the case of skin cutting.

In the following, non-limiting embodiments of the present invention, the main elements of the absorbent article are described.

The absorbent article according to the present invention comprising three main elements: the topsheet, facing the user of the article during use and being preferably liquid pervious in order to allow liquids, particularly body fluids, to pass into the article; the backsheet, providing liquid containment such that absorbed liquid does not leak through the article, this backsheet conventionally provides the garment facing surface of the article; and the absorbent element sandwiched between the topsheet and the backsheet and providing the absorbent capacity of the article to acquire and retain liquid which has entered the article through the topsheet.

Absorbent Element

The absorbent element as meant herein is any element of the article, except the topsheet and backsheet, which have fluid handling properties, including but not limited to, distribution, transfer, wicking, absorption and/or retention properties. According to the present invention, the absorbent element can include the following components: (a) an optional primary fluid distribution layer, preferably together with optional additional fluid distribution layers; (b) a fluid storage layer; (c) an optional fibrous layer underlying the storage layer.

One optional component of the absorbent element according to the present invention is a primarily fluid distribution layer. The primarily fluid distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent article.

Besides the primarily fluid distribution layer additional optional distribution layers might be present. For example the also optional secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilized. The fluid distribution layers can be comprised of any material typical for such distribution layers. In particular fibrous layers maintain the capillaries between fibers even when wet and are useful as distribution layers.

Positioned in fluid communication with, and typically underlying the topsheet, or optional primary or secondary distribution layers if present, is a fluid storage layer. The fluid storage layer is an essential element of the absorbent element herein able to ultimately acquire and retain body fluid.

The fluid storage layer comprises as an essential element a liquid absorbent thermoplastic composition comprising a thermoplastic polymeric base material having particles of water-insoluble water swellable absorbent material dispersed therein, said composition being configured in a plurality of unattached spaced apart zones also called herein storage zones.

The liquid absorbent thermoplastic composition might be used for totally or partially substituting conventional fibrous storage layer comprising water swellable absorbent material. In a preferred embodiment of the present invention the storage layer consists of the liquid absorbent thermoplastic composition described herein configured in plurality of unattached spaced apart zones.

By 'plurality' it is meant two or more unattached zones. By 'unattached' it is meant herein that adjacent zones are individualized and separated from each other without any physical link. However it is understood herein that although said zones of the absorbent element are separate pieces of material they are operably/functionally assembled together. It is understood herein that said zones provide at least part or even preferably the whole liquid absorption and retention capacity of the absorbent element. Said zones that serve the function of absorbing and retaining the liquid, particularly body fluid, called herein also 'storage zones', are delimited per regions located and extending between immediately adjacent unattached spaced apart storage zones, said regions are free of said liquid absorbent thermoplastic composition and are called herein the 'liquid transport regions'. Said liquid transport regions help to more effectively and more rapidly distribute liquid, particularly body fluids, to the storage zones. Indeed when some storage zones are more wetted than other storage zones, e.g. the storage zones located at entry point of fluid discharge versus more remote storage zones, the operability of the liquid transport regions can continue to provide substantially unrestricted flow paths through the more wetted zones to the less wetted zones of the storage layer.

For example in typical absorbent articles body fluids primarily enter the absorbent element, namely the storage layer, at the target section of the absorbent article, and the storage zones in the target section can become wetted and even saturated prior to wetting and saturating the storage zones in sections of the absorbent element/storage layer that are relatively more remote from the target section. With the distinctive, controlled preservation of liquid transport regions, however, fluid can readily flow around and past the more wetted and swollen storage zones to reach the more remote, less wetted zones. As a result the complete absorbent capacity of substantially the entire storage layer can be more effectively used. The invention can advantageously provide a storage layer wherein the swelling of the storage zones in the target section of the article does not inhibit the flow of fluid to the storage zones outside the target section.

Also advantageously the wicking speed upon subsequent fluid loading is equal or even faster than upon first body fluid discharge, resulting in improved fluid acquisition and reduced rewetting occurrence. Without to be bound by any theory, it is speculated that this is most likely due to the fact that upon first contact with fluid the hydrophilicity of the overall absorbent element comprising the storage layer and optional fluid acquisition layer is enhanced, thereby enhancing the fluid handling properties of the absorbent element upon subsequent body fluid discharge.

The plurality of unattached spaced apart zones might be configured in any size as well as any type of shape and be provided via predetermined or random application methods on a substrate in the article. The zones might take any type of geometrical form being regular or irregular in shape, including but not limited to lines/channels or stripes being rectilinear or curved, dots, circles, squares, rectangles, triangles, lozenges, spirals and any combination thereof.

Preferably each of the unattached spaced apart storage zones can be configured to extend substantially continuously over an area of not less than 0.001 cm$^2$, preferably from 0.01 to 50 cm$^2$, more preferably from 0.5 to 20 cm$^2$, even more preferably from 1 to 10 cm$^2$ and most preferably from 2 to 5 cm$^2$ to provide storages zones having desired characteristics.

In addition the overall system of storage zones can be positioned and arranged in desired patterns to provide a selected operable zones array composed of the cooperating individual unattached spaced apart storage zones. The zones array, in one aspect of the present invention, can provide a pattern size having total surface area extend of not less than 1 cm$^2$, preferably from 1 to 200 cm$^2$, more preferably from 10 to 100 cm$^2$, and most preferably from 20 to 75 cm$^2$. By 'pattern size' it is meant herein total surface area covered per all unattached spaced apart zones without considering the interstitial area between said zones (also called herein the transport regions).

In particular aspects of the invention, there is a discrete separation distance between adjacent individual/unattached spaced apart zones. The zones spacing distance is at least 0.1 mm, preferably is from 0.5 to 10 mm, more preferably from 1 to 5 mm and most preferably from 1.2 to 3 mm to provide desired performance. If the separation distance between individual storage zones is too small, the fluid may not be able to move along and across the surfaces of the spaced apart zones of the storage layer at a sufficiently rapid rate. If the separation distance between individual storage zones is too big, the fluid may have the tendency to be localized and distributed between the spaced apart zones, without being effectively absorbed per said zones, thereby saturating the absorption capacity of the storage layer. Subsequent loading of fluid might not be absorbed/retained as effectively as the storage layer is already saturated. The whole absorbent capacity of the spaced apart zones might not be as effectively used.

Preferable pattern is such that the storage zones form continuous or discontinuous substantially parallel channels or stripes along the longitudinal axis (MD direction) of the article. Such parallel stripes guide the fluid transport to the elongated direction of the stripes. Such pattern is particularly advantageous as it contributes most in delivering optimum properties in respect to fluid distribution/wicking properties and hence overall fluid handling properties resulting in reduced rewet as well as enhanced flexibility to the article especially along transverse axis (CD direction).

Figure 2:
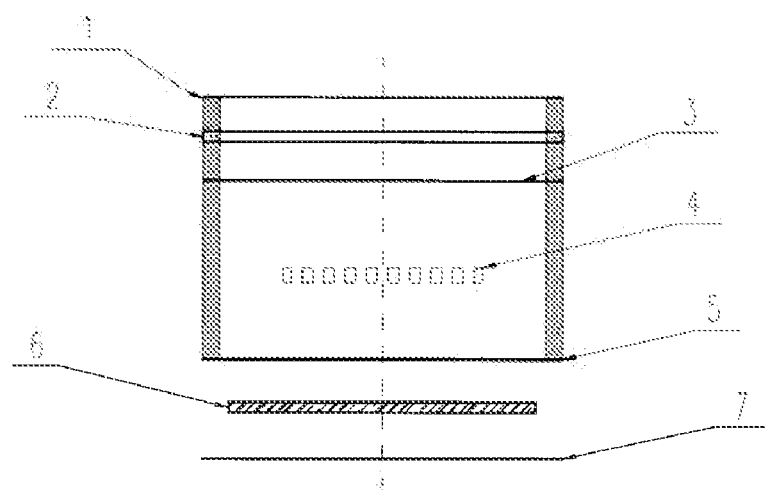
FIG. 2 is a side view of the panty liner of FIG. 1 taken through line D-D'.
Figure 3:
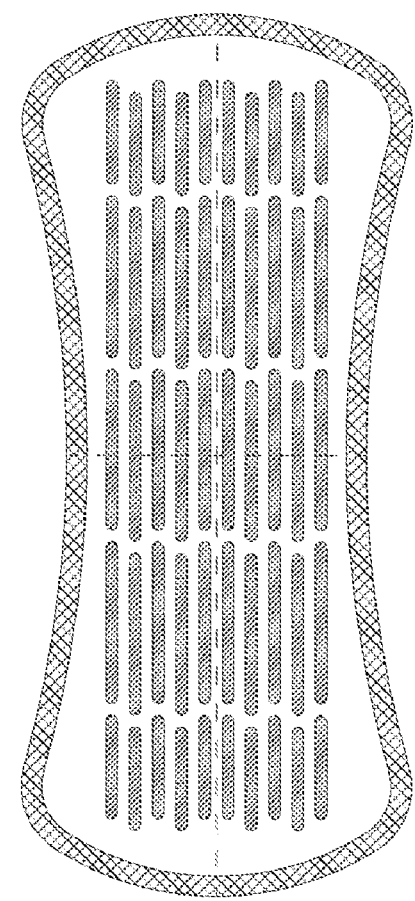
FIGS. 3-9 show top plan view of garment facing surface of alternative panty liners according to the present invention with storage layer made of liquid absorbent thermoplastic composition adhered to the backsheet of the liners in various patterns of a plurality of unattached spaced apart zones.
Figure 4:
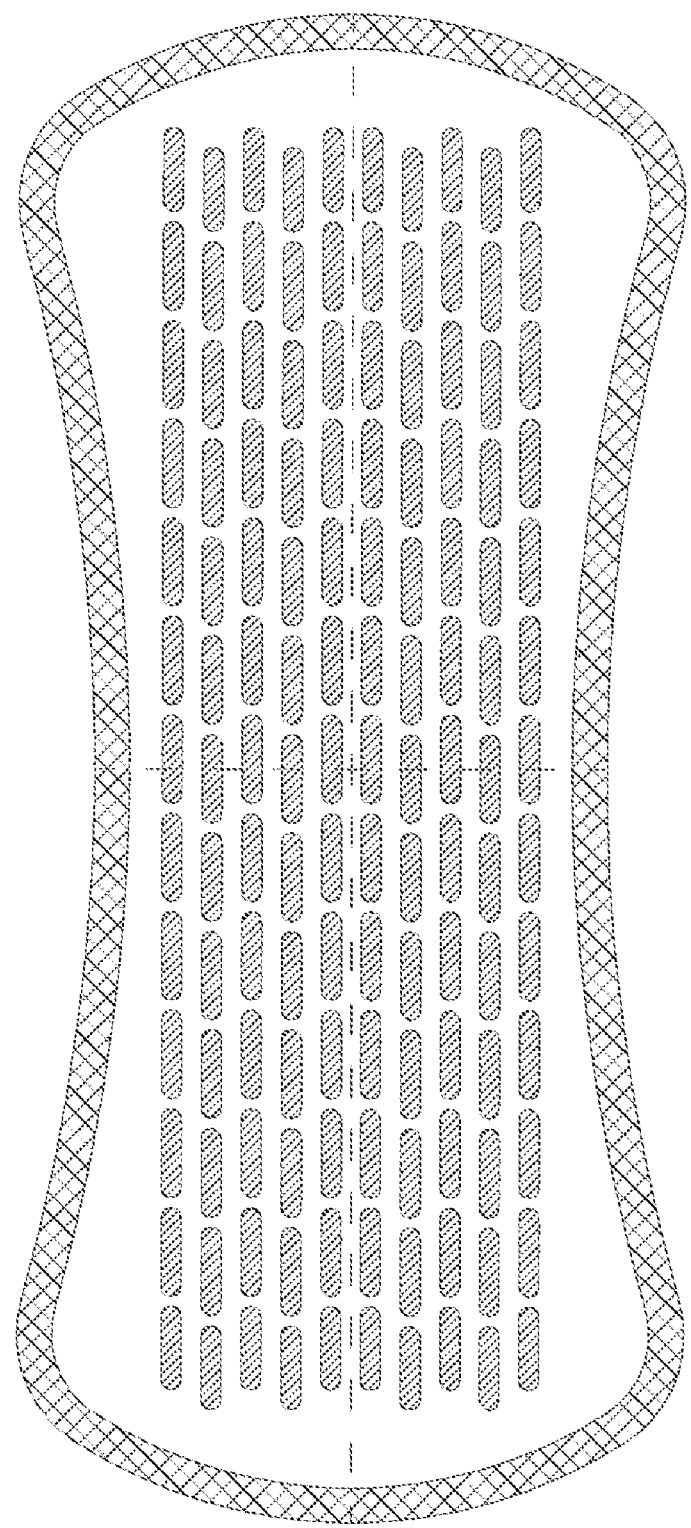
Figure 5:
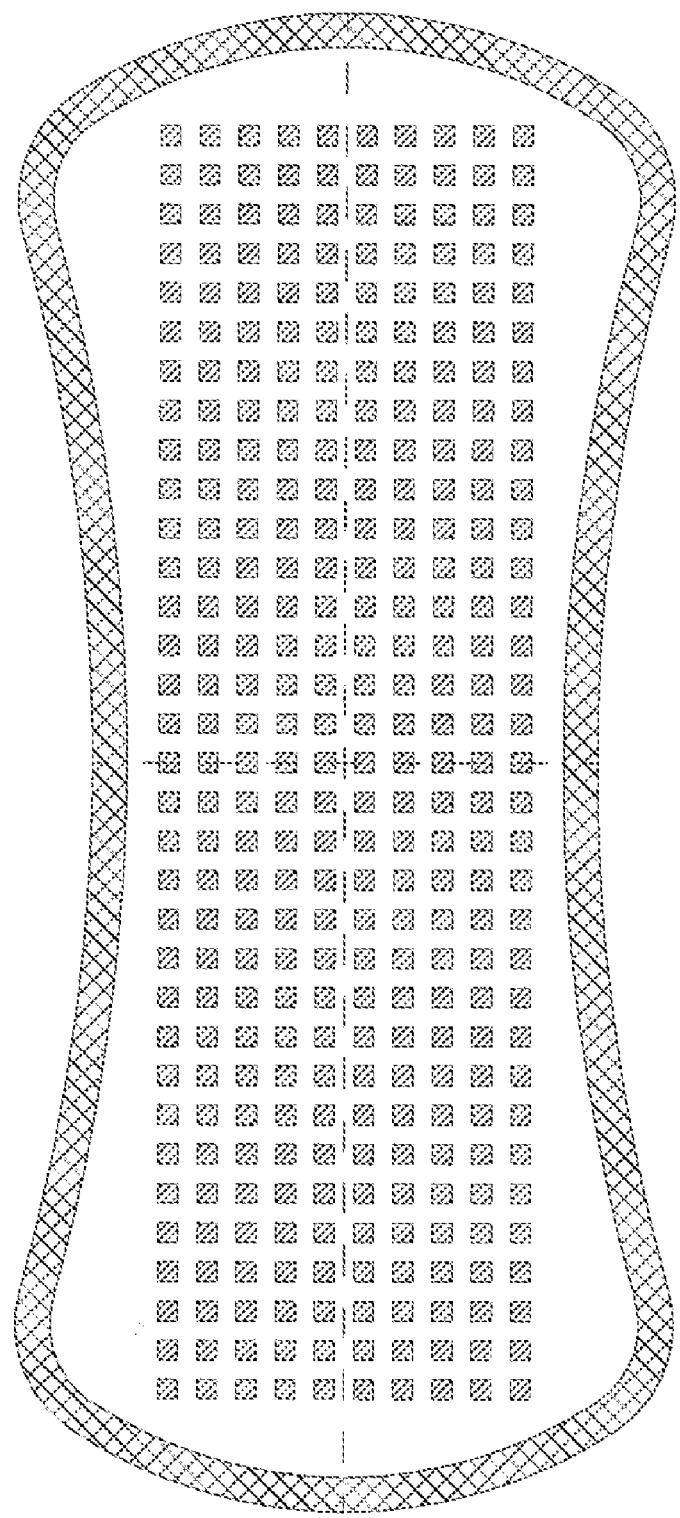
Figure 6:
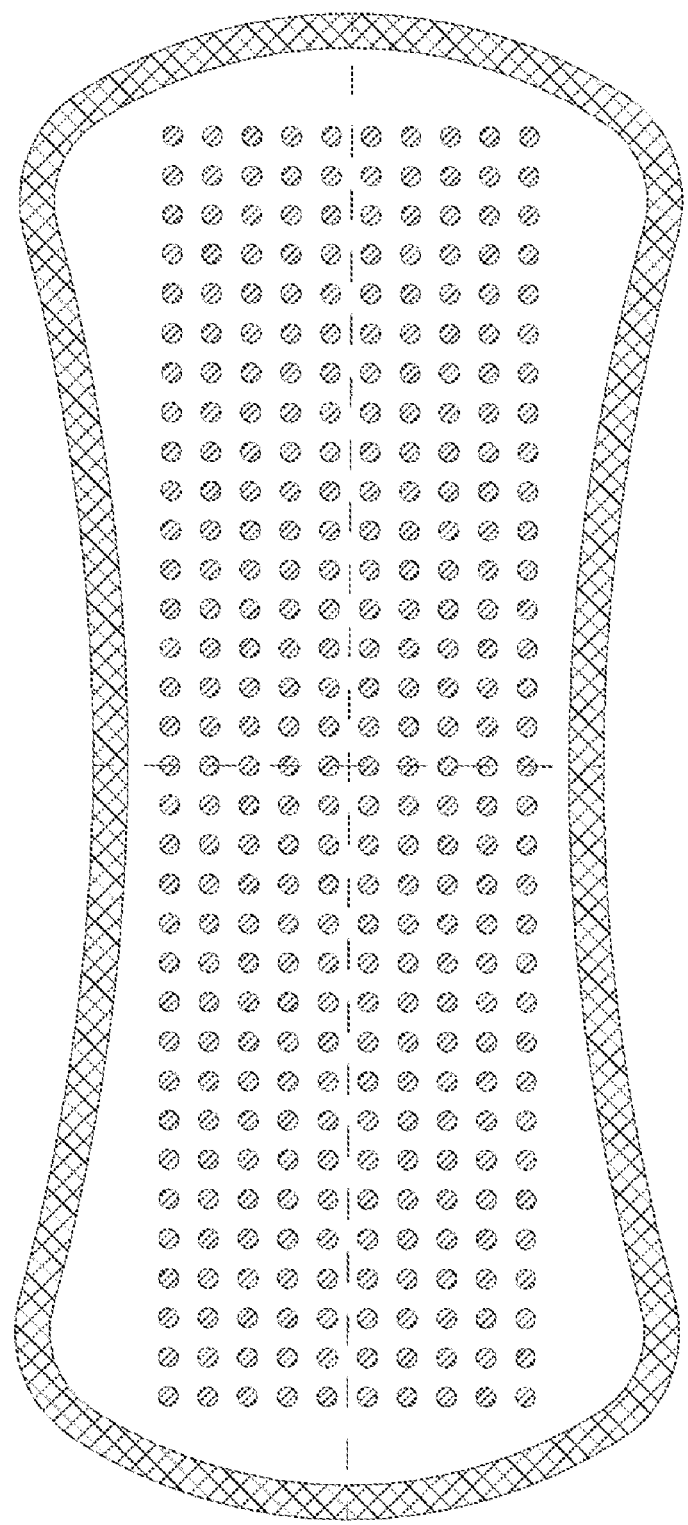
Figure 7:
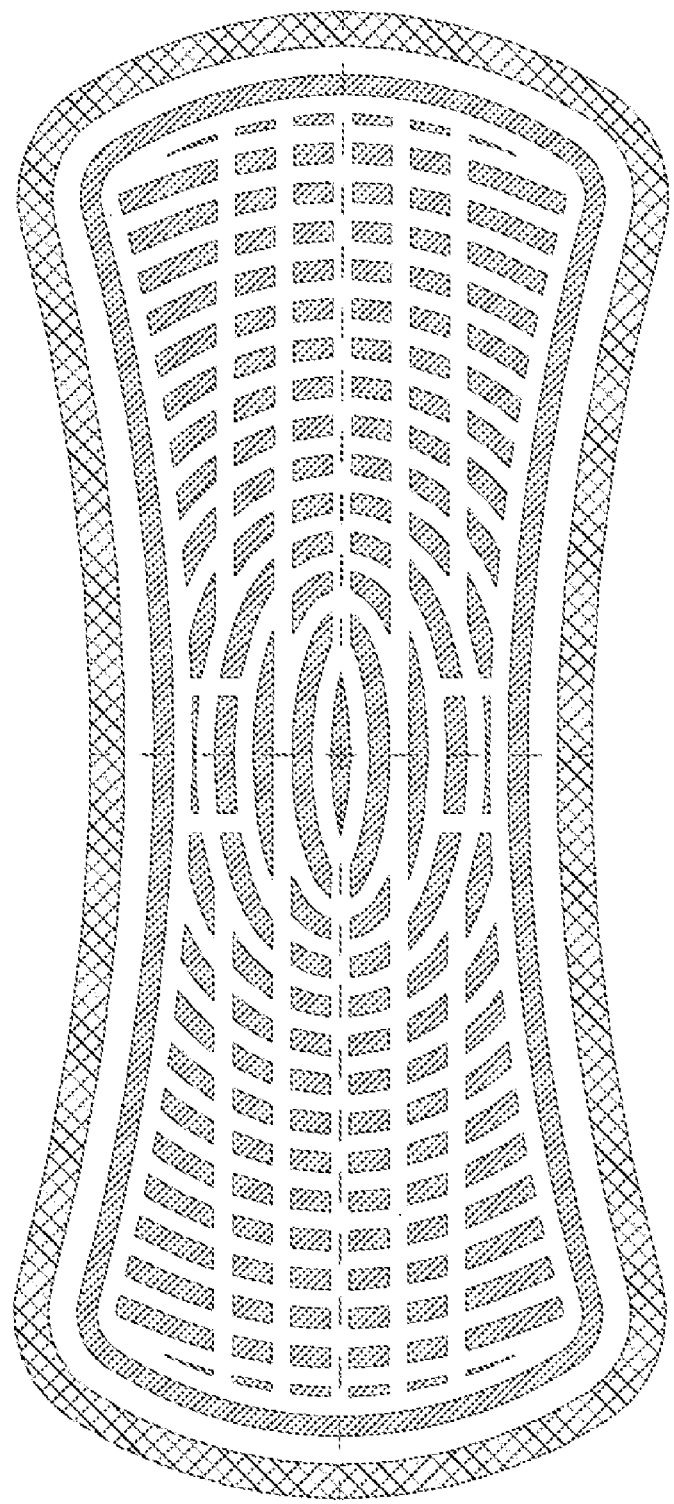
Figure 8:
Figure 9:
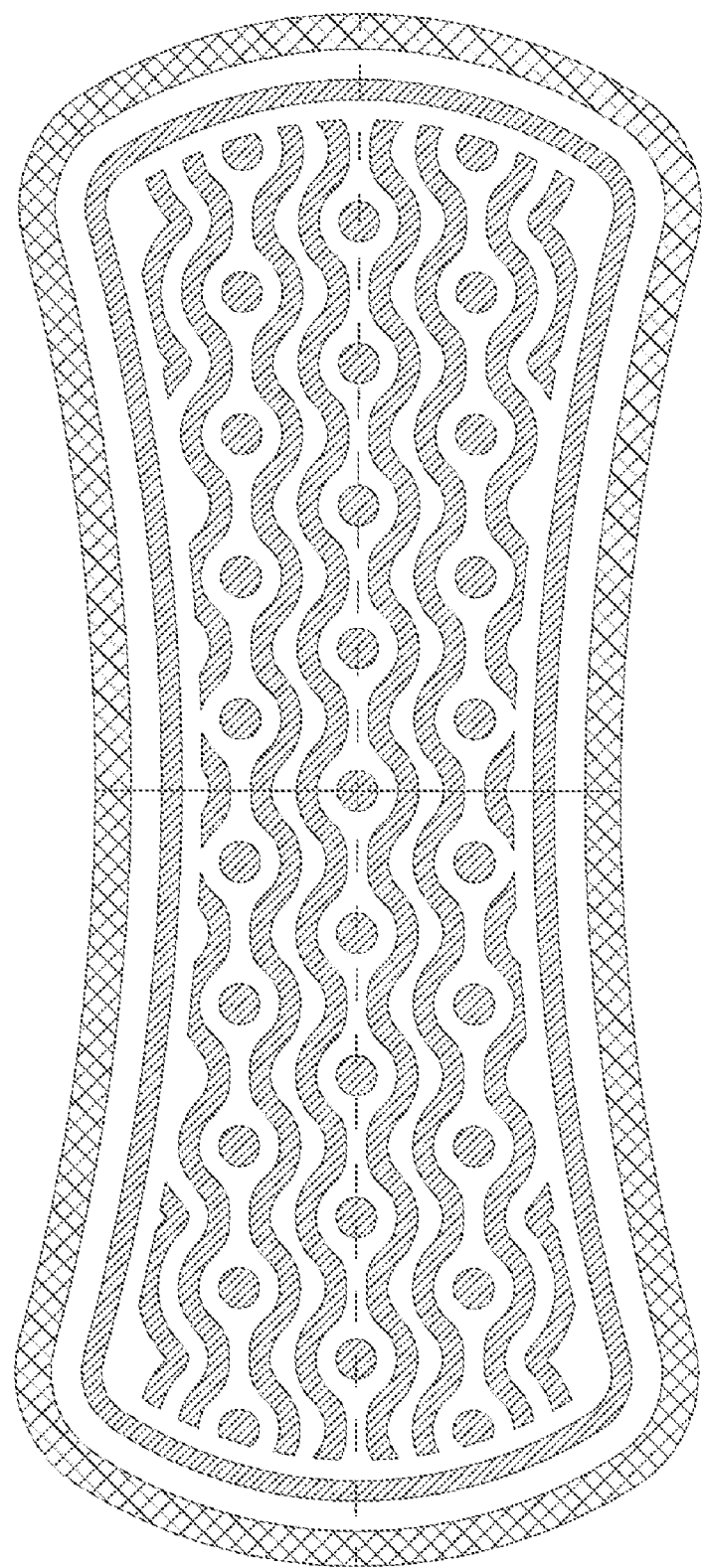

A particularly preferred pattern is illustrated in FIG. 1. FIG. 1 shows a pantyliner with a topsheet and backsheet being coextensive with each other and being attached to each other along the outer edge of the pantyliner per heat bonding C. This pantyliner comprises a storage layer with storage zones A that take the form of stripes delimiting liquid transport regions B. The width of the stripe 'a' can vary as desired. In FIG. 1 the width 'a' is about 2 mm and the distance separating two adjacent stripes 'b' is about 2 mm. FIG. 2 is a cross section of the pantiliner of FIG. 1 taken trough line D-D', said liner comprises a topsheet (1), an adhesive layer (2) for adhering the topsheet to the underlying fluid distribution layer (3), a storage layer (4), a backsheet (5) and adhesive layer (6) for adhering the backsheet (5) of the liner to a release liner (7). FIGS. 3 to 9 illustrate other pantyliners according to the present invention with alternative pattern of the plurality of spaced apart zones.

The use of such liquid absorbent thermoplastic composition configured in a plurality of spaced apart zones in the storage layer of the absorbent element of the absorbent articles herein provides outstanding liquid absorption capacity and liquid handling properties. More particularly due to capillary effects enhanced liquid distribution is obtained and the occurrence of gel blocking effect is reduced, resulting in enhanced liquid acquisition and retention with reduced soilage occurrence, especially when submitted to additional body fluid discharge upon prolonged wearing time. This results in reduced rewetting and enhanced dryness performance and hence improved overall comfort. All these benefits are obtained while not compromising on thinness and flexibility of the whole absorbent article, but even improving said characteristics.

Advantageously the thermoplastic composition also serves the purpose of fastening adhesive for attaching layers of the absorbent articles together, e.g., the backsheet to which the composition is typically adhered to, the topsheet or another layer if present like optional fluid distribution layer or optimal fibrous layer.

In one embodiment herein in order to realize the benefits of the present invention the storage layer comprises a liquid absorbent thermoplastic composition having a total absorption capacity towards saline solution of at least 2 grams per gram. Preferably the total absorption capacity of the composition towards saline solution is at least 5 g/g, more preferably at least 15 g/g and most preferably at least 20 g/g. The total absorption capacity of the composition used herein is determined in test mentioned hereinafter.

The articles of the present invention have a total liquid absorption capacity great enough to absorb small vaginal discharge during non menstruation of the wearer or even medium to high menstrual flow. In a preferred embodiment herein the absorbent element is such as the total liquid absorption capacity of the entire article is of at least 1 gram, preferably at least 2 to 80 grams, more preferably from 4 to 40 grams and most preferably from 6 to 30 grams when measured according to the dunk absorption capacity test described herein after.

Typically the storage layer provides more than 80% of the total absorption capacity of the article, preferably more than 90% and most preferably from 90% to 100%.

In one embodiment herein the absorbent element comprises the liquid absorbent thermoplastic composition described herein at a percent by weight of the total weight of the absorbent element of at least 15%, preferably from 20% to 100%, more preferably from 30% to 90%, even more preferably from 45% to 85% and most preferably from 55% to 80%.

Preferably the liquid absorbent thermoplastic composition represents at least 1% by weight of the total weight of the absorbent article, preferably from 5% to 90%, more preferably from 10% to 70%, even more preferably from 15% to 50% and most preferably from 20% to 40%.

The storage layer comprises particles of water-insoluble water swellable absorbent material dispersed homogeneously or non-homogeneously in a thermoplastic polymeric base material, as the suitable carrier.

Water-insoluble but water-swellable absorbent materials or absorbent gelling materials are usually referred to as "hydrogels", "super absorbent", "absorbent gelling" materials. Absorbent gelling materials are those materials that, upon contact with aqueous fluids, especially aqueous body fluids, imbibes such fluids and thus form hydrogels. These absorbent gelling materials are typically capable of absorbing large quantities of aqueous body fluids, and are further capable of retaining such absorbed fluids under moderate pressures. These absorbent gelling materials are typically in the form of discrete, non fibrous particles, even if super absorbent in fiber form are known.

Any commercially available super absorbent material in particle form is suitable for the present invention. Suitable absorbent gelling materials for use herein will most often comprise a substantially water-insoluble, slightly crosslinked, partially or fully neutralized, polymeric gelling material. This material forms a hydrogel upon contact with water. Such polymer materials can be prepared from polymerizable, unsaturated, acid-containing monomers. Suitable unsaturated acidic monomers for use in preparing the polymeric absorbent gelling material used in this invention include those listed in U.S. Pat. No. 4,654,039 and reissued as RE 32,649. Preferred monomers include acrylic acid, methacrylic acid, and 2-acrylamido-2-methyl propane sulfonic acid. Acrylic acid itself is especially preferred for preparation of the polymeric gelling material. The polymeric component formed from the unsaturated, acid-containing monomers can be grafted onto other types of polymer moieties such as starch or cellulose. Polyacrylate grafted starch materials of this type are especially preferred. Preferred polymeric absorbent gelling materials that can be prepared from conventional types of monomers include hydrolyzed acrylonitrile grafted starch, polyacrylate grafted starch, polyacrylates, maleic anhydride-based copolymers and combinations thereof. Especially preferred are the polyacrylates and polyacrylate grafted starch, but other absorbent substances in particle form such as inorganic materials ($MgSO_4$, $CaCl_2$, silicas, zeolites, etc.) or absorbing polymers (i.e. chitin derivatives such as, for example, chitosan) can be used alone but, preferably, blended with the above super absorbent polymers.

It is preferable that the particle size of the absorbent material used herein in dry state is below 150 micrometers, more preferably below 50 micrometers and most preferably from 40 to 10 micrometers. Small particle size are preferred herein as this results in optimum performance and processability for adhering the thermoplastic composition to the desired substrate. "Particle size" as used herein means the weighted average of the smallest dimension of the individual particles. Highly preferred water insoluble water swellable materials for use herein have a substantially angle-lacking shape and preferably have a spherical shape. Suitable commercially available absorbent gelling material is for example Aqua-keep® 10SH-NF, available from Sumitomo Seika, having an average particle size of between 20 μm and 30 μm.

It is preferable that the water insoluble water swellable absorbent material is present in an amount from 1% to 95%, preferably from 10% to 90%, more preferably from 30% to 70% and most preferably from 40% to 60% by weight of the total liquid absorbent thermoplastic composition.

The liquid absorbent thermoplastic composition for use herein besides the absorbent material further comprises as an essential element a polymeric base material typically at a level from 5% to 99%, preferably 10% to 90%, more preferably from 30% to 70%, most preferably from 40% to 60% by weight of the liquid absorbent thermoplastic composition.

Any polymeric base material known to the skilled person and conventionally used in the construction of absorbent articles, such as feminine care absorbent articles (e.g. sanitary napkins, panty liners or incontinence articles) or baby care absorbent articles (e.g. diapers) can be used herein. The polymeric base materials for use herein comprise thermoplastic polymers as an essential element. Thermoplastic polymer or mixtures of polymers are present in amounts typically ranging from about 5% to 99%, preferably 10% to 90%, more preferably from 30% to 70%, most preferably from 40% to 60% with respect to the total weight of the thermoplastic polymeric base material.

A variety of different thermoplastic polymers are suitable for use herein. Exemplary thermoplastic polymers include but are not limited to block copolymers, amorphous and crystalline polyolefins including homogeneous and substantially linear ethylene/alpha-olefin interpolymers, interpolymers of ethylene such as ethylene-vinyl-acetate (EVA), ethylene-methyl-acrylate (EMA) and ethylene n-butyl acrylate (EnBa) and mixtures thereof. The group of block copolymers includes linear copolymers of the triblock A-B-A or the diblock A-B type, or radial co-polymer structures having the formula $(A-B)_x$. The A blocks are non-elastic polymer blocks, typically polyvinylarene blocks, the B blocks are unsaturated conjugated dienes, such as poly(monoalkenyl) blocks, or hydrogenated versions thereof, x denotes the number of polymeric arms, and x is an integer greater than or equal to one. Suitable block A polyvinylarenes include, but are not limited to polystyrene, polyalpha-methylstyrene, polyvinyltoluene, and combinations thereof. Suitable block B poly(monoalkenyl) blocks include, but are not limited to conjugated diene elastomers such as for example polybutadiene or polyisoprene or hydrogenated elastomers such as ethylene butylene or ethylene propylene or polyisobutylene, or combinations thereof. Commercial examples of these types of block copolymers include Europrene™ Sol T from EniChem, Kraton™ elastomers from Shell Chemical Company, Vector™ elastomers from Dexco, Solprene™ from Enichem Elastomers and Stereon™ from Firestone Tire & Rubber Co.

Amorphous polyolefins or amorphous polyalphaolefins (APAO) are homopolymers, copolymers, and terpolymers of $C_2$-$C_8$ alphaolefins. These materials are typically polymerised by means of processes, which employ Ziegler-Natta catalysts resulting in a relatively broad molecular weight distribution. Commercially available amorphous polyalphaolefins include Rextac™ and REXFlex™ propylene based homopolymers, ethylene-propylene copolymers and butene-propylene copolymers available from Rexene (Dallas, Tex.) as well as Vestoplast alpha-olefin copolymers available from Huls (Piscataway, N.J.).

Metallocene polyolefins are homogeneous linear and substantially linear ethylene polymers prepared using single-site or metallocene catalysts. Homogeneous ethylene polymers are characterized as having a narrow molecular weight distribution and a uniform short-chain branching distribution. In the case of substantially linear ethylene polymers, such homogeneous ethylene polymers are further characterized as having long chain branching. Substantially linear ethylene polymers are commercially available from The Dow Chemical Company as Affinity™ polyolefin plastomers, which are produced using Dow's Insite™ technology, whereas homogeneous linear ethylene polymers are available from Exxon Chemical Company under the tradename Exact™. Homogeneous linear and substantially linear ethylene polymers having a relatively low density, ranging from about 0.855 to about 0.885, and a relatively low melt index, for example less than about 50 g/10 min are most preferred, particularly for creating elastomeric fibers, films and adhesive compositions that swell upon exposure to water.

The term 'interpolymer' is used herein to indicate a copolymer, terpolymer, or higher order polymer. That is, at least one other comonomer is polymerized with ethylene to make the interpolymer. Interpolymers of ethylene are those polymers having at least one comonomer selected from the group consisting of vinyl esters of a saturated carboxylic acid wherein the acid moiety has up to 4 carbon atoms, unsaturated mono- or dicarboxylic acids of 3 to 5 carbon atoms, a salt of the unsaturated acid, esters of the unsaturated acid derived from an alcohol having 1 to 8 carbon atoms, and mixtures thereof.

If employed uncompounded, the ethylene to unsaturated carboxylic comonomer weight ratio is preferably greater than about 3:1, more preferably about 2:1. Hence, the comonomer concentration is preferably greater than 30 wt-%, more preferably greater than 33 wt-% and most preferably greater than 35 wt-%, with respect to the total weight of the ethylene interpolymer. The melt index of the interpolymers of ethylene may range from about 50 to about 2000, preferably from about 100 to 1500, more preferably from about 200 to 1200, and most preferably from about 400 to 1200 g/10 min. When employing a polymer having too low of a melt index uncompounded, the strength of the polymer tends to constrain the swelling of the particles of super absorbent material.

Suitable ethylene/unsaturated carboxylic acid, salt and ester interpolymers include ethylene/vinyl acetate (EVA) ethylene/acrylic acid (EEA) and its ionomers; ethylene/methacrylic acid and its ionomers; ethylene/methyl acrylate (EMA); ethylene/ethyl acrylate; ethylene/n-butyl acrylate (EnBA); as well as various derivatives thereof that incorporate two or more comonomers.

Other suitable thermoplastic polymers that may be employed include polylactide, caprolactone polymers, and poly (hydroxy-butyrate/hydroxyvalerate), certain polyvinyl alcohols, biodegradable copolyesters such as Eastman Copolyester 14766 (Eastman), linear saturated polyesters such as Dynapol or Dynacoll polymers from Huls, poly (ethylene oxide) polyether amide and polyester ether block copolymers available from Atochem (Pebax™) or Hoechst Celanese (Rite-flex™) respectively, and polyamide polymers such as those available from Union Camp (Unirez™) or Huls (Vestamelt™) or EMS-Chemie (Griltex™). Other suitable thermoplastic polymers are e.g. polyurethanes, poly-ether-amides block copolymers, polyethylene-acrylic acid and polyethylene-methacrylic acid copolymers, polyethylene oxide and its copolymers, ethylene acrylic esters and ethylene methacrylic esters copolymers, polylactide and copolymers, polyamides, polyesters and copolyesters, polyester block copolymers, sulfonated polyesters, poly-ether-ester block copolymers, poly-ether-ester-amide block copolymers, ionomers, polyethylene-vinyl acetate with a vinyl acetate content of at least 28% by weight, polyvinyl alcohol and its copolymers, polyvinyl ethers and their copolymers, poly-2-ethyl-oxazoline and derivatives, polyvinyl pyrrolidone and its copolymers, thermoplastic cellulose derivatives, poly-caprolactone and copolymers, poly glycolide, polyglycolic acid and copolymers, polylactic acid and copolymers, polyureas, polyethylene, polypropylene, or mixtures thereof.

Particularly suitable preferred thermoplastic polymers are selected from thermoplastic poly-ether-amide block copolymers (e.g. Pebax™), thermoplastic poly-ether-ester-amide block copolymers, thermoplastic polyester block copolymers (e.g. Hytrel™), thermoplastic polyurethanes (e.g. Estane™), or mixtures thereof.

The polymeric base material for use herein preferably further comprise suitable compatible plasticizers. Plasticizers or mixture thereof are preferably present in amounts ranging from about 5% to 90%, preferably 10% to 80%, more preferably from 15% to 70% and most preferably from 30% to 65%, by weight, with respect to the total weight of the thermoplastic polymeric base material. Suitable 'plasticizers' for use herein generally will include any conventional plasticizers which decrease hardness and modulus, enhance pressure sensitive tack and reduce melt and solution viscosity. It is preferred that the plasticizer be water soluble or water dispersible or alternatively be a wax-like substance such as polyethylene or polypropylene glycol, glycerin, glycerol and its esters, butylene glycol or sorbitol. Other plasticizers suitable for use herein are esters of sucrose; phthalate plasticizers such as dioctyl phthalate and butyl benzyl phthalate (e.g., Santicizer 160 from Monsanto); benzoate plasticizers such as 1,4-cyclohexane dimethanol dibenzoate (e.g., Benzoflex 352 from Velsicol), diethylene glycol/dipropylene glycol dibenzoate (e.g., Benzoflex 50 from Velsicol), and diethylene glycol dibenzoate where the mole fraction of hydroxyl groups which have been esterified ranges from 0.5 to 0.95 (e.g., Benzoflex 2-45 High Hydroxyl also from Velsicol); phosphite plasticizers such as t-butyl diphenyl phosphate (e.g., Santicizer 154 from Monsanto); adipates; sebacates; epoxidized vegetal oils; polymerised vegetal oils; polyols; phthalates; liquid polyesters such as Dynacol 720 from Huls; glycolates; p-toluene sulfonamide and derivatives; glycols and polyglycols and their derivatives; sorbitan esters; phosphates; monocarboxylic fatty acids ($C_8$-$C_{22}$) and their derivatives; liquid rosin derivatives having Ring and Ball hydrocarbon oils which are low in aromatic content and which are paraffinic or naphthenic in character and mixtures thereof. Plasticizer oils are preferably low in volatility, transparent and have as little color and odor as possible. An example of a preferred plasticizer is Carbowax™ polyethylene glycol from Union Carbide. The use of plasticizers also contemplates the use of olefin oligomers, low molecular weight polymers, vegetable oils and their derivatives and similar plasticizing liquids.

Particularly preferred plasticizers to be used herein are hydrophilic plasticizers such as acids, esters, amides, alcohols, polyalcohols, or mixtures thereof, among which even more preferred are citric acid esters, tartaric acid esters, glycerol and its esters, sorbitol, glycolates, and mixtures thereof, as disclosed in our application WO 99/64505. Said preferred hydrophilic plasticizers have a particularly high polar character and provide the further advantage that they do not impair, and possibly can even enhance, the moisture vapor permeability of the resulting layer formed from the polymeric base material and thus the liquid absorbent thermoplastic composition used herein comprising said preferred plasticizer or blend of plasticizers, when compared to a corresponding layer formed from an liquid absorbent thermoplastic composition comprising the same components, but without such a plasticizer or plasticizers.

These particularly preferred hydrophilic plasticizer or blend of hydrophilic plasticizers can of course also adjust the viscosity of the polymeric base material and thus of the liquid absorbent thermoplastic composition to desirable values in order to help processable when adhering said composition onto a substrate.

According to a further even more preferred embodiment of the present invention, for avoiding migration of the plasticizer or blend of plasticizers from the matrix of thermoplastic polymeric base material it is preferable that the molecular weight (MW) of the selected plasticiser or plasticisers be greater than 300, preferably greater than 1000, and more preferably greater than 3000. Plasticisers having a MW of at least 6000 work particularly well.

As a matter of fact absorbent articles are assembled by and contain conventional hydrophobic hot melt adhesive which can interact with the absorbent material of the present invention and particularly with its hydrophilic plasticizer giving rise to a degradation of the adhesive characteristics of the conventional hot melt adhesive. For example, a sanitary napkin or a panty liner is generally made of a liquid permeable topsheet, of a liquid impermeable backsheet, and of an fibrous absorbent core there between. Generally the outside of the backsheet is provided with stripes of conventional hot melt pressure sensitive adhesive for fastening the absorbent article to the user's panty. If said conventional absorbent core is substituted in total or in part by a absorbent element made of the absorbent thermoplastic composition described herein, for example coated onto the inner surface of the backsheet, the inventors have surprisingly found that if the hydrophilic plasticiser or the blend of hydrophilic plasticisers are selected from those having a molecular weight (MW) greater than 300, preferably greater than 1000, more preferably greater than 3000, there is no interference with the adhesive for fastening the absorbent article, i.e. no peel reduction of said adhesive is experienced, while using hydrophilic plasticizers of lower molecular weight a significant reduction of adhesive peel is experienced, presumably due to plasticiser migration out of the liquid absorbing thermoplastic composition.

Most preferably, plasticisers having the preferred molecular weight as explained above can be selected from the group consisting of glycerol esters, sucrose esters, sorbitol, epoxidized vegetal oils, polymerised vegetal oils, polyalcohols, polyols, liquid polyesters, p-toluene sulfonamide and derivatives, polyglycols and their derivatives, monocarboxylic fatty acids ($C_8$-$C_{22}$) and their derivatives, and mixtures thereof, wherein polyglycols and their derivatives are particularly preferred (i.e. polyethylene glycols and polypropylene glycols).

The polymeric base material for use in the liquid absorbent thermoplastic composition herein optionally also comprises tackifying resins. Tackifying resins are preferably present in amounts ranging from about 0% to 100%, preferably 1% to 30%, more preferably from 5% to 20% and most preferably from 8% to 12% by weight of total weight of the thermoplastic polymeric base material. As used herein, the term 'tackifying resin' means any of the liquid absorbent thermoplastic compositions described below that are useful to impart tack to the polymeric base material. ASTM D1878-61T defines tack as "the property of a material which enables it to form a bond of measurable strength immediately on contact with another surface". Tackifying resins comprise resins derived from renewable resources such as rosin derivatives including wood rosin, tall oil and gum rosin as well as rosin esters, natural and synthetic terpenes and derivatives of such. Aliphatic, aromatic or mixed aliphaticaromatic petroleum based tackifiers are also useful in the invention. Representative examples of useful hydrocarbon resins include alpha-methyl styrene resins, branched and unbranched $C_5$ resins, $C_9$ resins and $C_{10}$ resins, as well as styrenic and hydrogenated modifications of such. Tackifying resins range from being a liquid at 37° C. to having a ring and ball softening point of about 135° C. Suitable tackifying resins for use herein include natural and modified resins; glycerol and pentaerythritol esters of natural and modified resins; polyterpene resins; copolymers and terpolymers of natural terpenes; phenolic modified terpene resins and the hydrogenated derivatives thereof; aliphatic petroleum resins and the hydrogenated derivatives thereof; aromatic petroleum resin and the hydrogenated derivatives thereof; and aliphatic or aromatic petroleum resins and the hydrogenated derivatives thereof, and combinations thereof. Commercial examples of these types of resins include Foral™ hydrogenated rosin ester, Staybelite™ hydrogenated modified rosin, Polypale™ polymerized rosin, Permalyn™ rosin ester, Pentalyn™ rosin ester, Adtac™ oil extended hydrocarbon resin, Piccopale™ aromatic hydrocarbon, Piccotac™, Hercotac™ aromatic modified aliphatic hydrocarbon, Regalrez™ cycloaliphatic resins, or Piccolyte™ from Hercules, Eselementz™ from Exxon Chemical aliphatic hydrocarbon and cycloaliphatic resins, Wingtack™ from Goodyear Tire & Rubber Co. synthetic polyterpene resins including aromatic modified versions, Arkon™ partially and fully hydrogenated aromatic resins from Arakawa Chemicals, Zonatac™ styrenated terpene resin, Zonarez™ rosin ester and Zonester™ rosin ester from Arizona Chemical and Nevtac™ aromatic modified aliphatic hydrocarbon from Neville Chemical Company.

The polymeric base material for use in the liquid absorbent thermoplastic composition herein optionally also comprises anti-oxidants. Antioxidant are typically present in amounts ranging from about 0.1% to 10%, preferably 0.2% to 5%, more preferably from 0.5% to 2%, most preferably from 0.75% to 1.5% by weight of total weight of the polymeric base material. Suitable 'anti-oxidants' for use herein include any conventional anti-oxidants, and are preferably hindered phenols such as for example Ethanox 330™ 1,3,5-trimethyl-2,4,6-tris(3,5-di-tert-butyl-4-hydroxybenzyl)benzene which is commercially available from the Ethyl Corporation. Other examples for suitable anti-oxidants are hindered phenolics (e.g., Irganox 1010, Irganox 1076).

The polymeric base material for use in the liquid absorbent thermoplastic composition herein optionally also comprises surfactants. Suitable 'surfactants' for use herein are additives that reduce the surface tension and/or contact angle of the polymeric base material. Surfactants are typically present in amounts ranging from about 0 wt-% to about 25 wt-% and preferably from about 5 wt-% to about 15 wt %, with respect to the total weight of the thermoplastic polymeric base material. Suitable surfactants include nonionic, anionic, and silicone surfactants. Exemplary nonionic surfactants are: Ethoxylates of (i) $C_1$-$C_{18}$, preferred $C_8$-$C_9$ alkyl or dialkyl phenols, such as those sold under the tradenames Macol DNP-10, available from PPG Industries, Gurnee, Ill., a 10 mole ethoxylate of dinonyl phenol, and Triton X-100, available from Union Carbide, a 10 mole ethoxylate of octyl phenol; (ii) alkyl $C_8$-$C_{60}$ monoalcohols, such as those sold under the tradenames Surfonic L-12-8, an 8 mole ethoxylate of dodecanol, available from Huntsman Chemical Co., and Unithox 480, a 38 mole ethoxylate crystalline surfactant available from Petrolite Specialty Polymers Group, Tulsa, Okla.; and (iii) propylene oxide polymers, such as those sold under the tradename Pluronic, which are ethylene oxide/propylene oxide block copolymers having a Mn of 200 to 3000, available from BASF; and benzoates formed by partial condensation of benzoic acid with hydrophilic di or mono-ols having less than 1000 Mn, such as the product of condensing about three equivalents of benzoic acid with four equivalent of diethylene glycol, commercially available as XP 1010 from Velsicol Chemical. A preferred nonionic surfactant blend is Atmer 685, available from ICI Surfactants (Wilmington, Del.). Suitable anionic surfactants are: $C_8$-$C_{60}$ alkyl ethoxylate sulfonates, $(CH_3—(CH_2)_{11-14}—(O—CH_2—CH_2)_3—SO_3^-Na^+$, such as, Avenel S30, available from PPG Industries; alkyl $C_8$-$C_{60}$ sulfonates, such as, Rhodapon UB $(C_{12}—SO_3^-Na^+)$ available from Rhone Poulenc; and alkyl/aromatic sulfonates, such as those sold under the tradename Calsoft. Suitable silicone surfactants are ethoxylates or propoxylates of polydimethyl siloxane, having a number average molecular weight of 500 to 10,000, preferably 600 to 6000, such as are sold under the tradenames Silwet L-77, L-7605, and L-7500 availablefrom OSi Specialties, Danbury, Conn.; and product 193 from Dow Corning. The preferred surfactants are those with lower molecular weights because these have increased compatibility in the polymeric base material. The maximum acceptable molecular weight depends on the type of surfactant and the other ingredients in the polymeric base material and thus the liquid absorbent thermoplastic composition.

Other optional components of the polymeric base material for use herein include anti-ultraviolets, dyes, antibacterials, odour adsorbing materials, perfumes, pharmaceuticals, and mixtures thereof, which may be present within the liquid absorbent thermoplastic compositions at a level of up to 20% by weight of the composition.

The liquid absorbent thermoplastic composition suitable for use herein is preferably a hot-melt adhesive, i.e. the polymeric base material comprises a hot-melt adhesive, which is capable of absorbing aqueous liquids. Such preferred liquid absorbent thermoplastic compositions comprise (by weight):

a) from about 5% to about 99% of a polymeric base material, comprising
  a') from about 10% to about 50% of a block copolymer,
  a'') from about 0% to about 50% of a tackifying resin;
  a''') from about 10% to about 80% plasticizer,
  a'''') from about 0% to about 2.0% antioxidant; and
b) from about 1% to about 95% of particles of water insoluble water swellable absorbent material.

Highly preferred thermoplastic polymeric base materials for use in the liquid absorbent thermoplastic compositions described herein before are those having a water absorption capacity of at least greater than 30%, preferably greater than 40%, more preferably greater than 60% and most preferably greater than 90%, when measured according to the Water Absorption Test described herein in accordance with ASTM D 570-81, on a film 200 μm thick. The intrinsic absorbency of the polymeric base material/matrix allows for a more effective diffusion of the body fluid within the matrix and, consequently, for a better spreading of the body fluid which can reach a greater number of absorbent material particles which in turn give rise to a better utilization of the absorbent material.

Highly preferred liquid absorbent thermoplastic compositions described herein before are those showing good integrity in wet state and hence having a tensile strength in wet state which is at least 20%, preferably at least 40%, and more preferably 60% of the tensile strength of said composition in dry state. Said tensile strengths are evaluated according to the Tensile Strength Test described herein. It should be appreciated that by selecting a thermoplastic base material, in the liquid absorbent thermoplastic composition herein having a higher value of water absorption, the absorbent composition will have better liquid absorption/handling characteristics, while not compromising on tensile strength in wet state. Indeed such absorbent composition will remain substantially intact and have sufficient tensile strength for its intended use, also upon liquid absorption.

Indeed the highly preferred liquid absorbent thermoplastic compositions for use herein offer improved mechanical and absorbent properties. Without to be bound by theory it is believed that the intrinsic absorbency of the matrix allows the body fluid to be acquired and diffused within the matrix thus permitting fluid contact with the absorbent material contained in the matrix and their swelling, without the necessity of having a matrix of low cohesive strength but with a matrix which remains substantially intact and having sufficient strength upon fluid absorption.

The absorbent in particle form or mixture thereof are blended with the polymeric base material in any known manner to provide the liquid absorbent thermoplastic composition for use herein. For example, by first melting the thermoplastic polymeric base material and then by adding and mixing the required amount of absorbent material particles. Suitable adhesive processing equipments can be used such as a melt mixer or extruder. Preferably the liquid absorbing thermoplastic compositions for use herein are formulated to have hot melt characteristics so that they can be applied utilizing any know method used for applying hot melt adhesives.

At least at the coating temperature, since the liquid absorbent thermoplastic composition comprises thermoplastic polymeric base materials, it can exhibit adhesive properties on a supportive substrate in order to form a composite structure such that no additional adhesive is required to achieve a permanent attachment between the absorbent element provided partially or preferably completely per the liquid absorbent thermoplastic composition, and the substrate. However, while hot melt techniques are preferred, any other known method for processing thermoplastic compositions can be used for processing the absorbent compositions in any known form/pattern. Also, any known method for spraying, printing, dotting, coating or foaming thermoplastic compositions can be used as well as extrusion, lamination processes.

Particularly suitable methods for applying the liquid absorbent thermoplastic composition to a substrate is per gravure printing or slot coating. Both methods are particularly suitable for discontinuous application of the thermoplastic composition described herein onto a substrate. Gravure print unit or slot coater apply the thermoplastic composition in the desired pattern onto a substrate.

Because the absorbent composition is thermoplastic, it allows for hot melt technique applications which in turn increase the versatility of its application in different form covering several distinct parts of whole surface of the layer substrate to which is applied to thereby providing the so called storage zones, typically the topsheet or backsheet or any intermediate layer directly adjacent the composition and interposed therebetween any of the outer surface of the article, i.e. topsheet and/or backsheet. The liquid absorbent composition can be provided covering discontinuously the article across its entire surface or it can cover only a region thereof, for example the central region of an article where body fluid is discharged in use. The total area of a surface onto which the liquid absorbent thermoplastic composition is applied to (preferably backsheet or any intermediate layers like fluid distribution layer if present or fibrous underlying layer if present) defines the actual absorbent surface of said composition in the absorbent article.

In one embodiment the totality of the plurality of unattached spaced apart zones represent as a minimum 8% of the total surface area of the absorbent article, when considering the plane surface occupied per the totality of said zones in respect to total plane surface area of the total article. Preferably the totality of the plurality of unattached spaced apart zones occupy a surface area which is from 15% to 90%, more preferably from 20% to 50% and most preferably from 25% to 40% of the total surface area of absorbent article.

An optional component for inclusion in the absorbent element according to the present invention is a fibrous layer adjacent to, and typically underlying the storage layer. If present this layer provides a substrate on which to deposit the liquid absorbent thermoplastic composition during manufacture of the absorbent element. If present such a layer typically provides some additional fluid-handling capabilities such as rapid wicking of fluid along the length of the absorbent article. Typically such a layer might be present if high capacity is desired like in the case of sanitary napkins for menstruation use. Such fibrous layer besides the transport regions is able to create additional void volume to handle and store temporary body fluids before being absorbed by the plurality of the spaced apart storage zones. In the case of liners for daily usage, where the total capacity and fluid handling properties needs are less demanding such layer is typically absent from the absorbent element and the thermoplastic composition is preferably adhered directly to the backsheet. Any material known to those skilled in the art might be used herein for the fibrous layer including but not limited to fibrous nowoven or woven material made of natural or synthetic fibers like polyolefines or cellulose.

Topsheet

The topsheet is compliant, soft feeling, and non-irritating to the wearer's skin. The topsheet also can be elastically stretchable in one or two directions. Further, the topsheet is preferably liquid pervious permitting body fluids to readily penetrate through its thickness.

A suitable topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. Suitable nonwoven materials/layers include fibrous nonwoven materials/layers formed by a carding process or a spunbond process or meltblown process whereby molten polymeric material is extruded through a die, attenuated to lengthen the extruded polymer into fibers and decrease the diameter thereof and is subsequently deposited on a forming surface. Methods of forming such nonwoven materials/layers are known to those skilled in the art. Polymeric materials suitable for use in forming such fibrous nonwoven materials/layers include polyolefins such as polyethylene and polypropylene, polyesters, nylons, ethylene vinyl acetate, ethylene methacrylate, copolymers of the above materials, block copolymers such as A-B-A block copolymers of styrene and butadiene, and the like.

Apertured formed films are especially preferred for the topsheet because they are pervious to body exudates and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. Nos. 3,929,135; 4,324,246; 4,342, 314; 4,463,045; and 5,006,394. Particularly preferred microapertured formed film topsheets are disclosed in U.S. Pat. Nos. 4,609,518 and 4,629,643. A preferred topsheet for the present invention is the apertured formed film described in one or more of the above patents and marketed on sanitary napkins by The Procter & Gamble Company of Cincinnati, Ohio as "DRI-WEAVE." The body surface of the formed film topsheet can be hydrophilic so as to help liquid to transfer through the topsheet faster than if the body surface was not hydrophilic. In a preferred embodiment, surfactant is incorporated into the polymeric materials of the formed film topsheet such as is described in U.S. patent application Ser. No. 07/794,745, filed on Nov. 19, 1991. Alternatively, the body surface of the topsheet can be made hydrophilic by treating it with a surfactant such as is described in the above referenced U.S. Pat. No. 4,950,254.

In yet an embodiment herein the topsheet is used together with an outer layer being directed towards the wearer surface. Such an outer layer is disposed onto the topsheet in a discontinuous way so that at least the region where liquid is expected to be discharged onto the absorbent article is free of the outer layer. Indeed, it is particularly preferred that the topsheet be a so-called hybrid topsheet in which the wearer contacting surface is provided in its longitudinal center by an apertured polymeric film or nonwoven while a region not including the center is provided with a non-woven such as e.g. the high loft non-woven or other non-woven which does provide particularly skin friendliness. Such hybrid topsheets have been disclosed in EPA-523 683, EP-A-523 719, EP-A-612 233, or EP-A-766 953.

Backsheet

The backsheet prevents the liquids absorbed and contained in the absorbent element from wetting articles that contact the absorbent article such as pants, pajamas and undergarments. The backsheet is preferably impervious to liquids like body fluids and is preferably manufactured from a thin plastic film, although other flexible liquid impervious materials can also be used. The backsheet needs to be compliant and will readily conform to the general shape and contours of the human body. The backsheet also can have characteristics allowing it to elastically stretch in one or two directions.

The backsheet can comprise a woven or nonwoven material, polymeric films such as thermoplastic films of polyethylene or polypropylene, or composite materials such as a film-coated nonwoven material.

Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance.

The backsheet typically extends across the whole of the absorbent element and can extend into and form part of or all of the preferred sideflaps, side wrapping elements or wings if such elements are present.

In addition to the prevention of liquid transport through the backsheet, the backsheet is preferably breathable. Hence the backsheet also permits the transfer of water vapor and preferably both water vapor and air through it and thus allows reduction of humid and occlusive environment on the skin contacted with the article. Advantageously the articles of the present invention, provided with a breathable backsheet, exhibit outstanding dry feeling both in dry and wet conditions and hence further enhanced comfort. Indeed the absorbent element according to the present invention comprising the liquid absorbent thermoplastic composition configured in unattached spaced apart zones as described herein significantly increases both the air and the water vapor permeability of the article during both dry and wet conditions. For example in wet condition a recovering of more than 80% of the original air permeability has been observed with articles according to the present invention (e.g., with the article exemplified in FIGS. 1 and 2, the recovering was of about 90%). Indeed it is speculated that after fluid discharge the transport regions transfer the fluid to the storages zones, thereby maintaining void space which results in reduction of the occlusion effect that normally occurs with conventional core materials/design.

Suitable breathable backsheets for use herein include all breathable backsheets known in the art. Suitable for use herein are single layer breathable backsheets which are breathable and impervious to liquids or dual layer backsheet, which in combination provide both breathability and liquid imperviousness.

Suitable single layer breathable backsheets for use herein include those described for example in GB A 2184 389, GB A 2184 390, GB A 2184 391, U.S. Pat. Nos. 4,591,523, 3,989, 867, 3,156,242 and WO 97/24097.

Suitable apertured formed films include films which have discrete apertures which extend beyond the horizontal plane of the garment facing surface of the layer towards the core thereby forming protuberances. The protuberances have an orifice located at their terminating ends. Preferably said protuberances are of a funnel shape, similar to those described in U.S. Pat. No. 3,929,135. Preferably said apertured preformed films are uni directional such that they have at least substantially, if not complete one directional fluid transport towards the absorbent element. Suitable macroscopically expanded films for use herein include films as described in for example in U.S. Pat. Nos. 637,819, 4,591,523, 4,637,819 and 4,591, 523.

Suitable monolithic films include Hytrel™, available from DuPont Corporation, USA, and other such materials as described in Index 93 Congress, Session 7A "Adding value to Nonwovens", J-C. Cardinal and Y. Trouilhet, DuPont de Nemours International S.A., Switzerland.

Suitable breathable backsheets for use herein are made of a first and a second layer. The first layer is positioned between the garment facing surface of the absorbent element and the wearer facing surface of the second layer/outer layer. It is oriented such that it retards or prevents liquid from passing from the absorbent element towards the outside while allowing free air flow and water vapor through it. The second layer provides water vapor and air permeability so as to support breathability of the article. In addition to water vapor permeability the air permeability is desirable in order to further improve the comfort benefit from the breathability of the article. Such a first layer provides air and water vapor permeability by being apertured. Preferably this layer is made in accordance with the aforementioned U.S. Pat. No. 5,591,510 or PCT WO 97/03818, WO 97/03795. In particular, this layer comprises a polymeric film having capillaries. Using a monolithic polymer film as the material for the first layer provides water vapor permeability even under stress conditions. While the apertures provide air permeability during "leakage safe" situations but close the capillaries under stress conditions the monolithic material maintains water vapor permeability in such a case. Preferred breathable monolithic film materials for use herein are those having a high vapor exchange.

In one embodiment herein the backsheet is made of a first layer of a resilient, three dimensional web which consists of a liquid impervious polymeric film having apertures forming capillaries which are not perpendicular to the plane of the film but are disposed at an angle of less than 90° relative to the plane of the film, and a second breathable layer (outer layer) of a porous web which is a fibrous nonwoven composite web of a meltblown nonwoven layer made from synthetic fibers having a basis weight of less than 28, preferably less than 13 $g/m^2$ and of a spunbonded nonwoven layer made from synthetic fibers.

The backsheet typically forms the garment facing surface on which the panty fastening adhesive is placed. Panty-fastening-adhesives can comprise any adhesive or glue used in the art for such purposes with pressure-sensitive adhesives being preferred.

According to the present invention the absorbent article may find utility as sanitary napkins, panty liners, adult incontinence products, nursing pads, baby diapers and the like. The present invention finds particular susceptibility as sanitary napkins and panty liners. A new product design, which is a sub-form of a sanitary napkin or panty liner form, namely thong shaped sanitary napkins or panty liners, so called thong liners, are included herein too.

Optionally, the absorbent articles of the present invention can comprise all those components typical for the intended product use. For example absorbent articles can comprise components such as wings in order to improve their positioning and soiling protection performance especially towards the rear end of the article. Such designs are shown for example in EP 130 848 or EP 134 086, Thong liners with wings are shown in U.S. design 394,503, UK designs 2,076,491 and 2,087,071 as well as internationally filed industrial model DM 045544, filed under the Hague Agreement, registered on Oct. 21, 1998.

Irrespective whether the wings are specially designed for thong liners or for conventional absorbent articles they can be provided as separate pieces and be attached to the thong liner or conventional pantiliners or sanitary napkins, or they can be integral with the materials of the absorbent articles, e.g. by being integral extension of the topsheet, the backsheet or a combination thereof. If the wings are attached then they can be attached in a basic outward pointing position or already be predisposed towards their in-use position, i.e. towards the longitudinal centerline.

The thickness of the absorbent article of the present invention especially for panty liners is less than 3 mm, more preferably in the range of 0.5 to 1.5 mm and even most preferably in the range of 0.8 to 1.3 mm according to the thickness measurement method described herein below.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Test method for total absorption capacity of the liquid absorbent thermoplastic composition The total liquid absorption capacity of the liquid absorbent thermoplastic composition is determined as follows:

Principle:

The sample is weighed and submerged in the test solution for 10 minutes and afterwards weighted to determine the total absorption capacity.

Preparation of Saline Solution:

(9±0.1) g NaCl (saline solution 0.9%) is added to deionized water to give a total mass of 1000 g±0.1 g and stirred until dissolved.

Apparatus and materials:

1. Bag (100×50 mm) heatsealable polyester mesh, folded and heat sealed on two (longer) of the three open sides so the inside edges of the seals are about 3 to 5 mm from the edge of the bag. Polyester mesh characteristic: Mass per unit area: 48 $g/m^2$, Thickness: 60 µm, Holes dimension: 18 µm, Open area: 13%, Yarn diameter: 31 µm, Number of yarn: 200/cm. Suggested supplier: Saatitech (www.saati.com); Reference material: PES18/13
2. Heat sealer capable of bonding polyester.
3. Analytical balance, capable of measuring a mass of 100 g to an accuracy off 0.001 g.
4. Weigthing silicon paper.
5. Timer.
6. Beaker capable of containing 1 liter of solution.
7. Spatula.
8. Tweezers.

Sample Preparation

Starting from an absorbent article the liquid absorbent thermoplastic composition can be isolated with knwon means in order to be tested. Typically in an absorbent article the topsheet is removed from the backsheet and both are separated from any additional layers if present. The liquid absorbent thermoplastic composition is scraped with a spatula from its substrate layer. The recovered thermoplastic composition will be used to prepare samples as mentioned below with known means. For example, the thermoplastic composition can be melted, or dissolved with a suitable solvent. The recovered composition must be kept in a closed container to avoid dust contamination and be allowed to equilibrate to the temperature to run the test. The test conditions are 23° C.±2° C. and 50±10% relative humidity.

Procedure

1. Weigh 0.200 g±0.005 g of the liquid absorbent thermoplastic composition and record the mass (Wd).
2. Prepare a sufficient number of bags (i.e., 6) to run the required replicates.
3. Place each single test portion of 0.200 g±0.005 g of the liquid absorbent thermoplastic composition into each single bag and seal the bags opened side.
4. Prepare two blank bags (i.e. without any composition) and test alongside the bags containing the thermoplastic composition.
5. Fill the beaker with 0.9% saline solution.
6. Submerge the bags in the saline solution. Eliminate entrapped air bubbles by manipulation of the bag.
7. After 10 minutes (±10 seconds), remove the bags from saline solution and hang them freely to drain vertically till no liquid is dripping from them.

8. Weigh each single bag recording the masses of the two blanks (Wb) 1 and 2 and the masses of bags containing the absorbent composition (Ww) 1, 2, . . . n.

Calculation and Results

Calculate the average of the two wet blank bags masses after absorption $$Wb=(Wb1+Wb2)/2$$

For each sample calculate:

$$Abs\ (g/g)=(Ww-Wb-Wd)/Wd$$

Where:
Wd=dry test portion mass in g.
Wb=average of 2 blank bag masses (after absorption) in g.
Ww=mass of wet bag containing liquid absorbent thermoplastic composition in g.

Dunk absorption capacity test for absorbent article

Purpose

This method measures the weight of a test fluid (Synthetic Urine B) which is retained in an absorbent article after it is immersed in the test fluid for a certain period of time and after applying a static pressure of 17 g/cm$^2$ on the article for 2 minutes.

Equipment

| Item | Supplier |
| --- | --- |
| Magnetic stirrer, with a top plate of 100 mm diameter | IKAMAG or equivalent |
| Magnetic stirring bar 64 mm | IKAMAG or equivalent |
| Beaker, 2000 ml capacity | Hirshmann or equivalent |
| Digital balance - accurate ±0.01 g | Mettler or equivalent |
| Timer control (stop watch) accurate to 0.5 sec | Mali or equivalent |
| Plexyglas plate and basin (at least 2 cm deep), at least 25 × 25 cm | Fisher or equivalent |
| Plexyglas slope with 15° angle to the horizontal, at least 8 cm wide | Convenient source |
| Weight of 1320 (±15 g) with base dimensions of 15.5 × 5 cm (equivalent to 17 g/cm$^2$) with a foam base covered with plastic film | Convenient source |
| Weight of 2265 g (±15 g) with base dimensions of 20.5 cm × 6.5 cm with a foam base covered with plastic film (for absorbent article with large dimensions, e.g. long wings) | Convenient source |
| A stand with an extendable arm to fix the weight on the slope and stop it from sliding | Convenient source |

Preparation of Synthetic Urine B Solution

Place a 2000 ml beaker on the balance. Weigh 800 g of demineralised water into the beaker. Carefully add into the beaker exact amounts of the following materials:

| | |
| --- | --- |
| 1) UREA (NH$_2$CO NH$_2$) | 20.00 grams |
| 2) Sodium Chloride (NaCl) | 9.00 grams |
| 3) Magnesium Sulfate (Mg So$_4$7H$_2$O) | 1.10 grams |
| 4) Calcium Chloride (CaCl$_2$2H$_2$O) | 0.79 grams |

Fill up to 1000 ml with mineralised water and mix the chemicals with aid of stemming bar on a magnetic stirrer. The resulting solution should be covered with parafilm to prevent evaporation or contamination.

Test Procedure

The following precautions should be followed during the test to ensure consistent accuracy of the results:

The absorbent article should be kept flat without bending or twisting in all steps of the test The article should be held gently at the top while the load is applied to prevent it from sliding. Applying the load should be done carefully and gradually starting from the top of the sample Ensure that the slope and base of the weight are dry before placement of the article. Also ensure that the balance tray is dry before weighing the wet absorbent article.

Pre-weigh the absorbent article (including release paper) using the digital balance and record the 'initial dry weight' to an accuracy of ±0.01 g.

Fill the basin partially with Syn. Urine B solution and ensure that the depth of the solution in the basin throughout the test is maintained higher than 5 mm.

Put the absorbent article face down in the basin for 25 minutes

Gently remove the absorbent article from the basin by holding it from its edge. Allow it to drip for 2 seconds in a vertical position, then place it face down on the slope with angle 15°.

Figure 10:
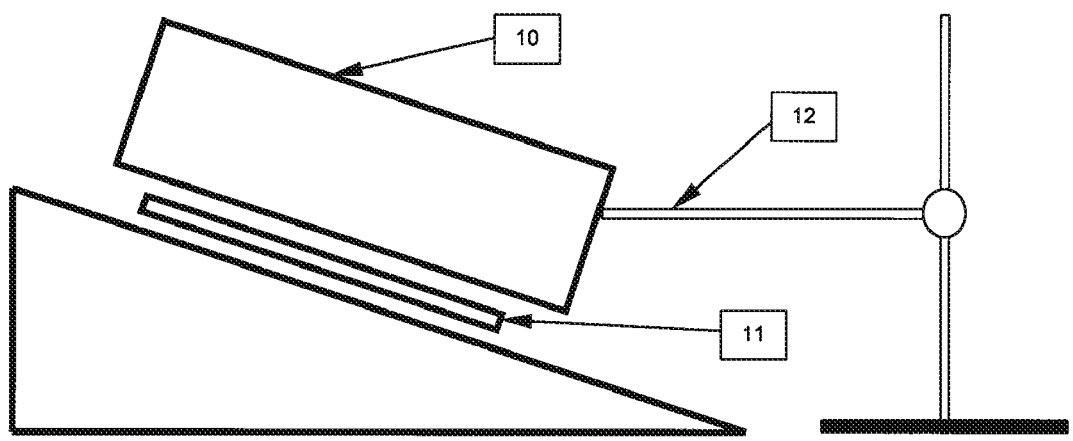
FIG. 10 shows the equipment for Dunk absorption test

Place the weight (10) gently on the article (11) for two minutes (±5 sec) and use the arm (12) of the stand to fix the weight (FIG. 10).

Remove the weight after the 2 minutes and hold the article from the edge and allow it to drip in a vertical position for two seconds, then re-weigh it and record the 'wet weight' to an accuracy of ±0.01 g.

Calculation of capacity (Dunk)

$$Dunk\ (g)=wet\ weight\ (g)-the\ initial\ dry\ weight\ (g)$$

The absorption capacity reported for a given absorbent article is the average of the Dunk value measured on at least 6 absorbent articles.

The absorption capacity can be reported in grams per square cm of the absorbent article tested as well as in grams per gram of absorbent article tested if desired.

Thickness Measurement

The thickness should always be measured at the thickest possible place, usually in the center of the absorbent article. For convenience the measurement is conducted on the absorbent article inclusive any protective cover means present. The product should be reconditioned at 50% humidity and 23° C. for two hours within its usual package and be removed not more than five minutes prior to the measurement.

The thickness is measured with a micrometer gauge having a range of 0 to 30 mm and capable of plus minus 0.5 mm tolerance. The gauge must not be spring loaded and should have a foot moving downwards under gravity. The micrometer foot has a diameter of 40 mm and is loaded with a 80 gram weight. The measurement is taken between 5 and 10 seconds after the foot has been lowed to come into contact with the absorbent article. Measurements should be taken often enough to allow statistical analysis to determine average thickness within a sigma of plus minus 0.1 mm. A detailed description of the thickness measurement can also be found in U.S. Pat. No. 5,009,653.

Water Absorption Test

The determination of the water absorption of thermoplastic polymeric base material used in preferred embodiment herein is conducted according to the standard test method ASTM D 570-81 with the following conditions. The measurement of water absorption for thermoplastic polymeric base material is made on a sample of the material in form of a film 76.2 mm long by 25.4 mm wide by 0.2 mm thick. For all materials a 24 hours immersion in distilled water at 23° C. is chosen and the percentage of water absorbed in accordance with the ASTM D 570-81 standard is reported.

Tensile Strength Test

The test measures the mechanical resistance of a sample of material as tensile strength at break, according to the standard test method ASTM D 412-92, under the following conditions. The test is performed on samples made of the liquid absorbent thermoplastic composition and having a length of 130 mm, a width of 25.4 mm, and a thickness of 2 mm, and being continuous, obtained with any suitable method, for example by pouring the liquid absorbent thermoplastic composition in molten state at a suitable temperature, e.g. 180° C. for the compositions of Examples 2 or 3, into a metallic pan lined with release paper in a continuous layer having a thickness of 2 mm, and then after cooling cutting from this layer the samples of the desired dimensions.

The test is performed on samples made of the same composition both in dry and in wet state. In order to prepare the samples in wet state a sample is placed in a container of a saline solution (e.g. 0.9% NaCl distilled water solution) maintained at a temperature of 23±1° C., and shall rest entirely immersed for ten minutes. At the end of ten minutes, the sample shall be removed from the water, all surface water wiped off with a dry cloth, and tested for wet tensile strength as provided in the standard test method.

Sample Preparation

When starting from an absorbent article comprising the liquid absorbent thermoplastic composition in turn comprising the matrix of thermoplastic polymeric base material with particles of water-insoluble water-swellable absorbent material dispersed therein, for example a disposable absorbent article with the thermoplastic composition coated onto a substrate, the thermoplastic composition can be isolated with known means in order to be tested. Typically in a disposable absorbent article the topsheet is removed from the backsheet and both are separated from any additional layers if present. The liquid absorbent thermoplastic composition is scraped with a spatula from its substrate layer. The recovered thermoplastic composition will be used to prepare samples as mentioned above with known means. For example, the thermoplastic composition can be melted, or dissolved with a suitable solvent. Particles of absorbent material can be also separated from the thermoplastic composition, in order to isolate the thermoplastic polymeric base material, as it is known in the art, for example by suitably sieving or filtering from the molten state, or preferably from the solution.

Examples for the liquid absorbent thermoplastic composition according to the present invention are as follow:

EXAMPLE 1

A liquid absorbent thermoplastic composition representative of present invention is following mixture, forming a hot-melt adhesive:

| 18% | Estane T5410 from Noveon |
|---|---|
| 17% | PEG E400 from Dow Chemical |
| 1% | Irganox B 225 from Ciba Speciality Chemicals |
| 19% | CR00 (former PM17) from Savare |
| 45% | Aquakeep 10 SH-NF ® from Sumitomo-Seika. |

Estane T5410 is a polyurethane-hydrophilic thermoplastic polymer, PEG E 400 is a polyethylene glycol (plasticizer, MW about 400), Irganox B 225 an anti oxidant and CR 00 is commercially available adhesive hotmelt.

EXAMPLE 2

A thermoplastic polyether-amide block copolymer available from Atofina (France) under the trade name Pebax MV 3000 is compounded with polyethylene glycol PEG 400 (plasticiser, MW about 400), Sodium Dodecyl Sulphate, both available from Aldrich Co., and Irganox B 225 (anti oxidant agent) available from Ciba-Geigy. The formulation in percent by weight has the following composition, and constitutes the thermoplastic polymeric base material:

| 28.6% | Pebax MV 3000 |
|---|---|
| 68.6% | PEG 400 |
| 1.4% | SDS |
| 1.4% | Irganox B 225 |

The thermoplastic polymeric base material has a water absorption of 43%, value measured according to the Water Absorption Test described herein. The thermoplastic base material is formed into a film to be used in the Water absorption Test by melt coating the thermoplastic base material at a temperature of 180° C. onto a release paper to obtain a film having the prescribed thickness of 200 μm. After cooling at room temperature the film is separated from the release paper.

A superabsorbent material in particle form, sold under the trade name Aqua Keep 10SH-NF by Sumitomo Seika Chemical (Japan) (average particle size between 20 and 30 μm and being in form of spherical beads), is added to the thermoplastic polymeric base material while maintained at a temperature of 180° C. and uniformly dispersed, in an amount corresponding to 42.9% by weight of the above thermoplastic polymeric base material. This example of the liquid absorbent thermoplastic composition has the following final composition by weight:

| 20% | Pebax MV 3000 |
|---|---|
| 48% | PEG 400 |
| 30% | Aqua Keep 10SH-NF |
| 1% | SDS |
| 1% | Irganox B 225 |

EXAMPLE 3

A thermoplastic polyether-ester block copolymer available from Du Pont (USA) under the trade name Hytrel 8171 is compounded with polyethylene glycol PEG 400 (plasticiser, MW about 400), polyethylene glycol PEG 1500 (plasticiser, MW about 1500), both available from Aldrich Co., and Irganox B 225 (anti oxidant agent) available from Ciba-Geigy. The formulation in percent by weight has the following composition, and constitutes an alternative thermoplastic polymeric base material:

| 28.6% | Hytrel 8171 |
|---|---|
| 21.4% | PEG 400 |
| 48.6% | PEG 1500 |
| 1.4% | Irganox B 225 |

The thermoplastic polymeric base material has a water absorption of 96%, value measured according to the Water Absorption Test described herein. The thermoplastic base material is formed into a film to be used in the Water absorption Test by melt coating the thermoplastic base material at a temperature of 180° C. onto a release paper to obtain a film having the prescribed thickness of 200 μm. After cooling at room temperature the film is separated from the release paper.

A superabsorbent material in particle form sold under the trade name Aqua Keep 10SH-NF by Sumitomo Seika Chemical (Japan) is added to the thermoplastic polymeric base material while maintained at a temperature of 180° C. and uniformly dispersed, in an amount corresponding to 42.9% by weight of the thermoplastic polymeric base material. As another illustrative example of the present invention, the resulting liquid absorbent thermoplastic composition has the following final composition by weight:

| | |
|---|---|
| 20% | Hytrel 8171 |
| 15% | PEG 400 |
| 34% | PEG 1500 |
| 30% | Aqua Keep 10SH-NF |
| 1% | Irganox B 225 |

All these compositions (Examples 1 to 3) have respectively a tensile strength in wet state which is at least 35% of the tensile strength of the composition in dry state, when evaluated according to the Tensile strength test described herein. All these compositions (Examples 1 to 3) have respectively a total absorption capacity towards saline solution (0.9%) of more than 5 grams per gram when measured according to test described herein before.

Examples of absorbent articles according to the present invention are described herein after:

EXAMPLE 4

A panty liner as illustrated in FIGS. 1 and 2 comprises an apertured polyethylene formed film topsheet (1) (code name X-28278 available from Tredegar), a spiral layer of adhesive (2) (D3151 available from Fuller), an absorbent element made of a fluid distribution nonwoven material (3) (carded bico Sawabond VP40/01/11 available from Sandler) together with a storage layer (4) consisting of plurality of spaced apart zones of a liquid absorbent thermoplastic composition of Example 1 above (basis weight of 152 g/m$^2$), said zones having the form of stripes of 2 mm width, a plastic polyethylene film backsheet (5) without pigment (code 14/18020, available from RKW), panty fastening adhesive (6) (HL1461 available from Fuller) and release liner (7). The topsheet, the fluid distribution layer and backsheet are substantially coextensive with each other and are attached to each other along the outer edge of the so-formed napkin by heat bonding C.

The total absorption capacity of this pantiliner as measured per Dunk absorption test described herein is of 7 grams towards Synthetic urine B.

In this pantiliner the liquid absorbent thermoplastic composition of Example 1 configured in stripes represents 75% by weight of the total weight of the absorbent element (i.e., fluid distribution layer and storage layer).

EXAMPLE 5

A sanitary napkin comprises an apertured polymeric film topsheet (CPM RIS coded 1035025 available from Tredegar, as the fluid distribution layer a 40 g/m$^2$ BICO thermalbonded carded nonwoven (coded Sawabond 4313) from Sandler underlying the topsheet, a storage layer made of stripes of the liquid absorbent thermoplastic composition of Example 2 above and a polyethylene backsheet (coded RKPA) from RKW. The topsheet, the fluid distribution layer and backsheet are substantially coextensive with each other and are attached to each other along the outer edge of the so-formed napkin by heat bonding.

EXAMPLE 6

A sanitary napkin as in Example 5, said napkin comprising in addition to the element mentioned in Example 5a fibrous layer underlying the storage layer, i.e., between the storage layer and the backsheet. This fibrous layer is a spunlaced nowoven layer.

The total absorption capacity of the sanitary napkin of Examples 5 and 6 as measured per Dunk absorption test described herein towards Synthetic urine B is of more than 10 grams. In the sanitary napkin of Example 6 the liquid absorbent thermoplastic composition of Example 2 configured in stripes represents 65% by weight of the total weight of the absorbent element (i.e., fluid distribution layer, storage layer and fibrous layer).

Other examples illustrating the present invention include for example the pantiliner of Example 4, wherein the liquid absorbent thermoplastic composition used is either the one of Examples 2 or 3 instead of the one of Example 1 above as well as the sanitary napkin of Example 5 or 6, wherein the liquid absorbent thermoplastic composition used is either the one of Example 1 or 3 instead of the one of Example 2.

All documents cited in the Detailed Description of the invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising
   a topsheet
   a backsheet
   and an absorbent element positioned between the topsheet and the backsheet, the absorbent element comprising a liquid absorbent thermoplastic composition which comprises a polymeric base material having particles of water-insoluble water swellable absorbent material dispersed therein, wherein the liquid absorbent thermoplastic composition has a total absorption capacity of at least 2 grams per gram and is configured in a first zone and a second zone that is spaced apart from the first zone by a distance of between 0.5 mm and 10 mm.

2. The absorbent article of claim 1, wherein the polymeric base material comprises a polyglycol.

3. The absorbent article of claim 1, wherein the water-insoluble water swellable absorbent material comprises a starch.

4. The absorbent article of claim 1, wherein the polymeric base material comprises a polyglycol and the water-insoluble water swellable absorbent material comprises a starch.

5. The absorbent article of claim 1, wherein the water-insoluble water swellable absorbent material is present in an amount from 30% to 70% by weight of the total liquid absorbent thermoplastic composition.

6. The absorbent article of claim 1, wherein the water-insoluble water swellable absorbent material is present in an amount from 40% to 60% by weight of the total liquid absorbent thermoplastic composition.

7. The absorbent article of claim 1, wherein the liquid absorbent thermoplastic composition is devoid of a tackifying resin.

8. The absorbent article of claim 1, wherein the first and second zones are in the form of stripes being rectilinear or curved, dots, circles, squares, rectangles, triangles, lozenges, spirals and their combination.

9. An absorbent article comprising
a topsheet
a backsheet
and an absorbent element positioned between the topsheet and the backsheet, the absorbent element comprising a liquid absorbent thermoplastic composition which comprises a polymeric base material having particles of water-insoluble water swellable absorbent material dispersed therein, wherein the liquid absorbent thermoplastic composition is configured in a plurality of unattached spaced apart zones and is devoid of a tackifying resin.

10. The absorbent article of claim 9, wherein the polymeric base material comprises a polyglycol.

11. The absorbent article of claim 9, wherein the water-insoluble water swellable absorbent material comprises a starch.

12. The absorbent article of claim 9, wherein the polymeric base material comprises a polyglycol and the water-insoluble water swellable absorbent material comprises a starch.

13. The absorbent article of claim 9, wherein the water-insoluble water swellable absorbent material is present in an amount from 30% to 70% by weight of the total liquid absorbent thermoplastic composition.

14. The absorbent article of claim 9, wherein the water-insoluble water swellable absorbent material is present in an amount from 40% to 60% by weight of the total liquid absorbent thermoplastic composition.

15. The absorbent article of claim 9, wherein the first and second zones are in the form of stripes being rectilinear or curved, dots, circles, squares, rectangles, triangles, lozenges, spirals and their combination.

16. The absorbent article of claim 9, wherein the liquid absorbent thermoplastic composition has a total absorption capacity of at least 1 gram per gram.

17. An absorbent article comprising
a topsheet
a backsheet
and an absorbent element positioned between the topsheet and the backsheet, the absorbent element comprising a liquid absorbent thermoplastic composition which comprises a polymeric base material having particles of water-insoluble water swellable absorbent material dispersed therein, wherein the water-insoluble water swellable absorbent material comprises a starch, and wherein the liquid absorbent thermoplastic composition is configured in a first zone and a second zone that is spaced apart from the first zone by a distance of between 0.5 mm and 10 mm.

18. The absorbent article of claim 17, wherein the polymeric base material comprises a polyglycol.

19. The absorbent article of claim 17, wherein the liquid absorbent thermoplastic composition has a total absorption capacity of at least 1 gram per gram.

20. The absorbent article of claim 17, wherein the liquid absorbent thermoplastic composition is devoid of a tackifying resin.

* * * * *